US011053525B2

(12) United States Patent
Jung et al.

(10) Patent No.: US 11,053,525 B2
(45) Date of Patent: Jul. 6, 2021

(54) MICROORGANISMS FOR PRODUCING PUTRESCINE OR ORNITHINE AND PROCESS FOR PRODUCING PUTRESCINE OR ORNITHINE USING THEM

(71) Applicant: CJ Cheiljedang Corporation, Seoul (KR)

(72) Inventors: Hee Kyoung Jung, Seoul (KR); Hye Won Um, Gyeonggi-do (KR); Hong Xian Li, Gyeonggi-do (KR); Su Jin Park, Seoul (KR); Young Lyeol Yang, Seoul (KR); Kyoung Min Lee, Gyeonggi-do (KR); Hyo Hyoung Lee, Incheon (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 131 days.

(21) Appl. No.: 15/739,699

(22) PCT Filed: Mar. 29, 2016

(86) PCT No.: PCT/KR2016/003198
§ 371 (c)(1),
(2) Date: Dec. 22, 2017

(87) PCT Pub. No.: WO2016/208854
PCT Pub. Date: Dec. 29, 2016

(65) Prior Publication Data

US 2018/0187222 A1 Jul. 5, 2018

(30) Foreign Application Priority Data

Jun. 24, 2015 (KR) ........................ 10-2015-0090021

(51) Int. Cl.

| | |
|---|---|
| ***C12N 1/20*** | (2006.01) |
| ***C12P 13/00*** | (2006.01) |
| ***C12P 13/10*** | (2006.01) |
| ***C12N 9/10*** | (2006.01) |
| ***C12N 9/88*** | (2006.01) |

(52) U.S. Cl.
CPC ................ *C12P 13/10* (2013.01); *C12N 1/20* (2013.01); *C12N 9/1018* (2013.01); *C12N 9/1025* (2013.01); *C12N 9/88* (2013.01); *C12P 13/001* (2013.01); *C12Y 201/03003* (2013.01); *C12Y 203/03001* (2013.01); *C12Y 401/01017* (2013.01)

(58) Field of Classification Search
None
See application file for complete search history.

(56) References Cited

U.S. PATENT DOCUMENTS

| | | | | |
|---|---|---|---|---|
| 2012/0214211 | A1 | 8/2012 | Bathe et al. | |
| 2013/0344545 | A1* | 12/2013 | Choi | C07K 14/34 435/114 |
| 2014/0134682 | A1* | 5/2014 | Wittmann | C12N 9/88 435/129 |
| 2015/0104838 | A1* | 4/2015 | Choi | C12N 9/1029 435/128 |

FOREIGN PATENT DOCUMENTS

| | | | | |
|---|---|---|---|---|
| CN | 1973037 | A | 5/2007 | |
| CN | 101679964 | A | 3/2010 | |
| CN | 104136600 | A | 11/2014 | |
| JP | 2009-254323 | A | 11/2009 | |
| JP | 2010506585 | A | 3/2010 | |
| JP | 2013544532 | A | 12/2013 | |
| JP | 2014500728 | A | 1/2014 | |
| KR | 10-0620092 | B1 | 9/2006 | |
| KR | 10-0924065 | B1 | 10/2009 | |
| KR | 10-2012-0064046 | A | 6/2012 | |
| KR | 10-2013-0082478 | A | 7/2013 | |
| KR | 20130082478 | A | 7/2013 | |
| KR | 10-1372635 | B1 | 3/2014 | |
| KR | 101372635 | B1 | 3/2014 | |
| KR | 10-2014-0115244 | A | 9/2014 | |
| WO | 2006/005603 | A1 | 1/2006 | |
| WO | 2006/065095 | A1 | 6/2006 | |
| WO | 2009/096689 | A2 | 8/2009 | |
| WO | 2009/125924 | A2 | 10/2009 | |
| WO | 2009/125992 | A2 | 10/2009 | |
| WO | WO-2013105827 | A2 * | 7/2013 | C12P 13/00 |
| WO | 2014/148743 | A1 | 9/2014 | |

OTHER PUBLICATIONS

UniProt Accession No. Q8NP85_CORGL, published Oct. 1, 2002 (Year: 2002).*
UniProt Accession No. CISY_CORGL, published Nov. 1, 1995 (Year: 1995).*
English Machine Translation of JP 2009-254323A, Abstract, Description and Claims, May 11, 2009 (Year: 2009).*
Blombach et al., "L-Valine Production during Growth of Pyruvate Dehydrogenase Complex-Deficient Corynebacterium glutamicum in the Presence of Ethanol or by Inactivation of the Transcriptional Regul . . . ," Applied and Environmental Microbiology 75(4): 1197-1200, Feb. 2009.
Database WPI (Derwent World Patent Index), Accession No. 2014-R60373, Oct. 29, 2014, two pages.

(Continued)

*Primary Examiner* — Richard C Ekstrom
(74) *Attorney, Agent, or Firm* — Cooley LLP

(57) ABSTRACT

The present invention relates to a recombinant microorganism for producing putrescine or ornithine, and a method for producing putrescine or ornithine using the same. Specifically, the present invention relates to a microorganism of the genus *Corynebacterium* capable of producing putrescine or ornithine, in which an activity of the transcriptional regulator of sugar metabolism (SugR) is weakened, an activity of the citrate synthase (GltA) is enhanced, or both are applied; and a method for producing putrescine or ornithine using the same.

32 Claims, No Drawings

Specification includes a Sequence Listing.

(56) References Cited

OTHER PUBLICATIONS

Engels et al., "The Global Repressor SugR Controls Expression of Genes of Glycolysis and of the L-Lactate Dehydrogenase LdhA in Corynebacterium glutamicum," Journal of Bacteriology 190(24): 8033-8044, Dec. 2008.
Gotoh et al., "Direct production of L-ornithine from casein by commercial digestive enzymes and in situ activated arginase," Bioprocess Biosyst Eng 33:773-777, 2010.
Jiang et al., "Metabolic engineering of Corynebacterium glutamicum for increasing the production of L-omithine by increasing NADPH availability, " J Ind Microbiol Biotechnol 40:1143-1151, 2013.
NCBI Blast Report: GenBank Protein Sequence, Accession No. Protein Sequence WP_011013914_1, Mar. 22, 2015, seven sheets.
NCBI Blast Report: GenBank Protein Sequence, Accession No. WP_ 011014761.1, Jul. 18, 2013, seven sheets.
NCBI Blast Report: GenBank Protein Sequence, Accession No. Protein Sequence WP_011015248_1, Jul. 18, 2013, seven sheets.
Qian et al., "Metabolic Engineering of Escherichia coli for the Production of Putrescine: A Four Carbon Diamine," Biotechnology and Bioengineering 104: 651-662, 2009.
Schneider et al., "Putrescine production by engineered Corynebacterium glutamicum," Appl Microbiol Biotechnol 88: 859-868, 2010.
Schneider et al., "Improving putrescine production by Corynebacterium glutamicum by fine-tuning ornithine transcarbamoylase activity using a plasmid addiction system," Appl Microbiol Biotechnol 95: 169-178, 2012.
Schiio et al., "Production of Aspartic Acid and Lysine by Citrate Synthase Mutants of Brevibacterium flavum," Agric. Biol. Chem. 46(1): 101-107, 1982.
Bartek et al., "Studies on Substrate Utilisation in L-valine-producing Corynebacterium Glutamicum Strains Deficient in Pyruvate Dehydrogenase Complex," Bioprocess Biosyst. Eng. 33:873-883 (2010).
Park et al., "Metabolic Engineering of Corynebacterium Glutamicum for L-Arginine Production," Nature Communications, 5(4618):1-9 (2014).
Zhan et al., "Cloning, Expression of the prpC2 Gene Encoding Citrate Synthase from Corynebacterium crenatum and Its Effect on L-arigine Synthesis," China Biotechnology 35(3):49-55 (2015).
Genbank No. CAF20272.1, "Transcriptional regulators of sugar metabolism, DeoR family [Corynebacterium glutamicum ATCC 13032]", dated Feb. 27, 2015, 2 pages.
Srere, "Controls of Citrate Synthase Activity," Life Sciences 15:1695-1710 (1974).

* cited by examiner

```
SEQUENCE LISTING

<160> NUMBER OF SEQ ID NOS: 51

<210> SEQ ID NO 1
<211> LENGTH: 259
<212> TYPE: PRT
<213> ORGANISM: Corynebacterium glutamicum ATCC13032

<400> SEQUENCE: 1

Met Tyr Ala Glu Glu Arg Arg Arg Gln Ile Ala Ser Leu Thr Ala Val
1               5                   10                  15

Glu Gly Arg Val Asn Val Thr Glu Leu Ala Gly Arg Phe Asp Val Thr
            20                  25                  30

Ala Glu Thr Ile Arg Arg Asp Leu Ala Val Leu Asp Arg Glu Gly Ile
        35                  40                  45

Val His Arg Val His Gly Gly Ala Val Ala Thr Gln Ser Phe Gln Thr
    50                  55                  60

Thr Glu Leu Ser Leu Asp Thr Arg Phe Arg Ser Ala Ser Ser Ala Lys
65                  70                  75                  80

Tyr Ser Ile Ala Lys Ala Ala Met Gln Phe Leu Pro Ala Glu His Gly
                85                  90                  95

Gly Leu Phe Leu Asp Ala Gly Thr Thr Val Thr Ala Leu Ala Asp Leu
            100                 105                 110

Ile Ser Glu His Pro Ser Ser Lys Gln Trp Ser Ile Val Thr Asn Cys
        115                 120                 125

Leu Pro Ile Ala Leu Asn Leu Ala Asn Ala Gly Leu Asp Asp Val Gln
    130                 135                 140

Leu Leu Gly Gly Ser Val Arg Ala Ile Thr Gln Ala Val Val Gly Asp
145                 150                 155                 160

Thr Ala Leu Arg Thr Leu Ala Leu Met Arg Ala Asp Val Val Phe Ile
                165                 170                 175

Gly Thr Asn Ala Leu Thr Leu Asp His Gly Leu Ser Thr Ala Asp Ser
            180                 185                 190

Gln Glu Ala Ala Met Lys Ser Ala Met Ile Thr Asn Ala His Lys Val
        195                 200                 205

Val Val Leu Cys Asp Ser Thr Lys Met Gly Thr Asp Tyr Leu Val Ser
    210                 215                 220
```

-continued

Phe Gly Ala Ile Ser Asp Ile Asp Val Val Val Thr Asp Ala Gly Ala
225 230 235 240

Pro Ala Ser Phe Val Glu Gln Leu Arg Glu Arg Asp Val Glu Val Val
245 250 255

Ile Ala Glu

<210> SEQ ID NO 2
<211> LENGTH: 780
<212> TYPE: DNA
<213> ORGANISM: Corynebacterium glutamicum ATCC13032

<400> SEQUENCE: 2
atgtacgcag aggagcgccg tcgacagatt gcctcattaa cggcagttga gggacgtgta 60
aatgtcacag aattagcggg ccgattcgat gtcactgcag agacgattcg acgagacctt 120
gcggtgctag accgcgaggg aattgttcac cgcgttcacg gtggcgcagt agccacccaa 180
tctttccaaa ccacagagtt gagcttggat actcgtttca ggtctgcatc gtcagcaaag 240
tactccattg ccaaggcagc gatgcagttc ctgcccgctg agcatggcgg actgttcctc 300
gatgcgggaa ctactgttac tgctttggcc gatctcattt ctgagcatcc tagctccaag 360
cagtggtcga tcgtgaccaa ctgcctcccc atcgcactta atctggccaa cgccgggctt 420
gatgatgtcc agctgcttgg aggaagcgtt cgcgcgatca cccaggctgt tgtgggtgac 480
actgcgcttc gtactctcgc gctgatgcgt gcggatgtag tgttcatcgg caccaacgcg 540
ttgacgttgg atcacggatt gtctacggcc gattcccaag aggctgccat gaaatctgcg 600
atgatcacca acgcccacaa ggtggtggtg ttgtgtgact ccaccaagat gggcaccgac 660
tacctcgtga gctttggcgc aatcagcgat atcgatgtgg tggtcaccga tgcgggtgca 720
ccagcaagtt tcgttgagca gttgcgagaa cgcgatgtag aagttgtgat tgcagaatga 780

<210> SEQ ID NO 3
<211> LENGTH: 257
<212> TYPE: PRT
<213> ORGANISM: Corynebacterium glutamicum ATCC13869

<400> SEQUENCE: 3

Met Tyr Ala Glu Glu Arg Arg Arg Gln Ile Ala Ser Leu Thr Ala Val
1 5 10 15

Glu Gly Arg Val Asn Val Thr Glu Leu Ala Gly Arg Phe Asp Val Thr
20 25 30

Ala Glu Thr Ile Arg Arg Asp Leu Ala Val Leu Asp Arg Glu Gly Ile
35 40 45

Val His Arg Val His Gly Gly Ala Val Ala Thr Gln Ser Phe Gln Thr
50 55 60

Thr Glu Leu Ser Leu Asp Thr Arg Phe Arg Ser Ala Ser Ser Ala Lys
65 70 75 80

Tyr Ser Ile Ala Lys Ala Ala Met Gln Phe Leu Pro Ala Glu His Gly
85 90 95

Gly Leu Phe Leu Asp Ala Gly Thr Thr Val Thr Ala Leu Ala Asp Leu
100 105 110

Ile Ser Glu His Pro Ser Ala Lys Gln Trp Ser Ile Val Thr Asn Cys
115 120 125

Leu Pro Ile Ala Leu Asn Leu Ala Asn Ala Gly Leu Asp Asp Val Gln
130 135 140

Leu Leu Gly Gly Ser Val Arg Ala Ile Thr Gln Ala Val Val Gly Asp

-continued

```
145                 150                 155                 160

Thr Ala Leu Arg Thr Leu Ala Leu Met Arg Ala Asp Val Val Phe Ile
                165                 170                 175

Gly Thr Asn Ala Leu Thr Leu Asp His Gly Leu Ser Thr Ala Asp Ser
            180                 185                 190

Gln Glu Ala Ala Met Lys Ser Ala Met Ile Thr Asn Ala His Lys Val
        195                 200                 205

Val Val Leu Cys Asp Ser Thr Lys Met Gly Thr Asp Tyr Leu Val Ser
    210                 215                 220

Phe Gly Ala Ile Ser Asp Ile Asp Val Val Val Thr Asp Ala Gly Ala
225                 230                 235                 240

Pro Ala Ser Phe Val Glu Gln Leu Arg Glu Arg Asp Val Glu Val Val
                245                 250                 255

Ile


<210> SEQ ID NO 4
<211> LENGTH: 780
<212> TYPE: DNA
<213> ORGANISM: Corynebacterium glutamicum ATCC13869

<400> SEQUENCE: 4

atgtacgcag aggagcgccg tcgacagatt gcctcattaa cggcagttga gggacgtgta      60

aatgtcacag aattagcggg ccgattcgat gtcactgcag agacgattcg acgagacctt     120

gcggtgctag accgcgaggg aattgttcac cgcgttcacg gtggcgcagt agccacccaa     180

tctttccaaa ccacagagtt gagcttggat actcgtttca ggtctgcatc gtcagcaaag     240

tactccattg ccaaggcagc gatgcagttc ctgcccgctg agcatggcgg actgttcctc     300

gatgcgggaa ctactgttac tgctttggcc gatctcattt ctgagcatcc tagcgccaag     360

cagtggtcga tcgtgaccaa ctgcctcccc atcgcactta atctggccaa cgccgggctt     420

gatgatgtcc agctacttgg aggaagcgtt cgcgcgatca cccaggctgt tgtgggtgac     480

actgcgcttc gtactctcgc gctgatgcgt gcggatgtag tgttcatcgg caccaacgcg     540

ttgacgttgg atcacggatt gtctacggcc gattcccaag aggctgccat gaaatctgcg     600

atgatcacca acgcccacaa ggtggtggtg ttgtgtgact ccaccaagat gggcaccgac     660

tacctcgtga gctttggcgc aatcagcgat atcgatgtgg tggtcaccga tgcgggtgca     720

ccagcaagtt tcgttgagca gttgcgagaa cgcgatgtag aagttgtgat tgcagaatga     780


<210> SEQ ID NO 5
<211> LENGTH: 437
<212> TYPE: PRT
<213> ORGANISM: Corynebacterium glutamicum ATCC13032

<400> SEQUENCE: 5

Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80
```

-continued

```
Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160

Leu Asp Glu Ala Gln Leu Asp Lys Ala Thr Val Arg Leu Met Ala Lys
                165                 170                 175

Val Pro Met Leu Ala Ala Tyr Ala His Arg Ala Arg Lys Gly Ala Pro
            180                 185                 190

Tyr Met Tyr Pro Asp Asn Ser Leu Asn Ala Arg Glu Asn Phe Leu Arg
        195                 200                 205

Met Met Phe Gly Tyr Pro Thr Glu Pro Tyr Glu Ile Asp Pro Ile Met
    210                 215                 220

Val Lys Ala Leu Asp Lys Leu Leu Ile Leu His Ala Asp His Glu Gln
225                 230                 235                 240

Asn Cys Ser Thr Ser Thr Val Arg Met Ile Gly Ser Ala Gln Ala Asn
                245                 250                 255

Met Phe Val Ser Ile Ala Gly Gly Ile Asn Ala Leu Ser Gly Pro Leu
            260                 265                 270

His Gly Gly Ala Asn Gln Ala Val Leu Glu Met Leu Glu Asp Ile Lys
        275                 280                 285

Ser Asn His Gly Gly Asp Ala Thr Glu Phe Met Asn Lys Val Lys Asn
    290                 295                 300

Lys Glu Asp Gly Val Arg Leu Met Gly Phe Gly His Arg Val Tyr Lys
305                 310                 315                 320

Asn Tyr Asp Pro Arg Ala Ala Ile Val Lys Glu Thr Ala His Glu Ile
                325                 330                 335

Leu Glu His Leu Gly Gly Asp Asp Leu Leu Asp Leu Ala Ile Lys Leu
            340                 345                 350

Glu Glu Ile Ala Leu Ala Asp Asp Tyr Phe Ile Ser Arg Lys Leu Tyr
        355                 360                 365

Pro Asn Val Asp Phe Tyr Thr Gly Leu Ile Tyr Arg Ala Met Gly Phe
    370                 375                 380

Pro Thr Asp Phe Phe Thr Val Leu Phe Ala Ile Gly Arg Leu Pro Gly
385                 390                 395                 400

Trp Ile Ala His Tyr Arg Glu Gln Leu Gly Ala Ala Gly Asn Lys Ile
                405                 410                 415

Asn Arg Pro Arg Gln Val Tyr Thr Gly Asn Glu Ser Arg Lys Leu Val
            420                 425                 430

Pro Arg Glu Glu Arg
        435
```

<210> SEQ ID NO 6
<211> LENGTH: 1314
<212> TYPE: DNA
<213> ORGANISM: Corynebacterium glutamicum ATCC13032

<400> SEQUENCE: 6
atgtttgaaa gggatatcgt ggctactgat aacaacaagg ctgtcctgca ctaccccggt 60

-continued

```
ggcgagttcg aaatggacat catcgaggct tctgagggta acaacggtgt tgtcctgggc    120
aagatgctgt ctgagactgg actgatcact tttgacccag gttatgtgag cactggctcc    180
accgagtcga agatcaccta catcgatggc gatgcgggaa tcctgcgtta ccgcggctat    240
gacatcgctg atctggctga gaatgccacc ttcaacgagg tttcttacct acttatcaac    300
ggtgagctac caaccccaga tgagcttcac aagtttaacg acgagattcg ccaccacacc    360
cttctggacg aggacttcaa gtcccagttc aacgtgttcc cacgcgacgc tcacccaatg    420
gcaaccttgg cttcctcggt taacattttg tctacctact accaggacca gctgaaccca    480
ctcgatgagg cacagcttga taaggcaacc gttcgcctca tggcaaaggt tccaatgctg    540
gctgcgtacg cacaccgcgc acgcaagggt gctccttaca tgtacccaga caactccctc    600
aatgcgcgtg agaacttcct gcgcatgatg ttcggttacc caaccgagcc atacgagatc    660
gacccaatca tggtcaaggc tctggacaag ctgctcatcc tgcacgctga ccacgagcag    720
aactgctcca cctccaccgt tcgtatgatc ggttccgcac aggccaacat gtttgtctcc    780
atcgctggtg gcatcaacgc tctgtccggc ccactgcacg gtggcgcaaa ccaggctgtt    840
ctggagatgc tcgaagacat caagagcaac cacggtggcg acgcaaccga gttcatgaac    900
aaggtcaaga acaaggaaga cggcgtccgc ctcatgggct tcggacaccg cgtttacaag    960
aactacgatc cacgtgcagc aatcgtcaag gagaccgcac acgagatcct cgagcacctc   1020
ggtggcgacg atcttctgga tctggcaatc aagctggaag aaattgcact ggctgatgat   1080
tacttcatct cccgcaagct ctacccgaac gtagacttct acaccggcct gatctaccgc   1140
gcaatgggct tcccaactga cttcttcacc gtattgttcg caatcggtcg tctgccagga   1200
tggatcgctc actaccgcga gcagctcggt gcagcaggca acaagatcaa ccgcccacgc   1260
caggtctaca ccggcaacga atcccgcaag ttggttcctc gcgaggagcg ctaa         1314
```

<210> SEQ ID NO 7
<211> LENGTH: 437
<212> TYPE: PRT
<213> ORGANISM: Corynebacterium glutamicum ATCC13869

<400> SEQUENCE: 7

```
Met Phe Glu Arg Asp Ile Val Ala Thr Asp Asn Asn Lys Ala Val Leu
1               5                   10                  15

His Tyr Pro Gly Gly Glu Phe Glu Met Asp Ile Ile Glu Ala Ser Glu
            20                  25                  30

Gly Asn Asn Gly Val Val Leu Gly Lys Met Leu Ser Glu Thr Gly Leu
        35                  40                  45

Ile Thr Phe Asp Pro Gly Tyr Val Ser Thr Gly Ser Thr Glu Ser Lys
    50                  55                  60

Ile Thr Tyr Ile Asp Gly Asp Ala Gly Ile Leu Arg Tyr Arg Gly Tyr
65                  70                  75                  80

Asp Ile Ala Asp Leu Ala Glu Asn Ala Thr Phe Asn Glu Val Ser Tyr
                85                  90                  95

Leu Leu Ile Asn Gly Glu Leu Pro Thr Pro Asp Glu Leu His Lys Phe
            100                 105                 110

Asn Asp Glu Ile Arg His His Thr Leu Leu Asp Glu Asp Phe Lys Ser
        115                 120                 125

Gln Phe Asn Val Phe Pro Arg Asp Ala His Pro Met Ala Thr Leu Ala
    130                 135                 140

Ser Ser Val Asn Ile Leu Ser Thr Tyr Tyr Gln Asp Gln Leu Asn Pro
145                 150                 155                 160
```

-continued

Leu Asp Glu Ala Gln Leu Asp Lys Ala Thr Val Arg Leu Met Ala Lys
165 170 175

Val Pro Met Leu Ala Ala Tyr Ala His Arg Ala Arg Lys Gly Ala Pro
180 185 190

Tyr Met Tyr Pro Asp Asn Ser Leu Asn Ala Arg Glu Asn Phe Leu Arg
195 200 205

Met Met Phe Gly Tyr Pro Thr Glu Pro Tyr Glu Ile Asp Pro Ile Met
210 215 220

Val Lys Ala Leu Asp Lys Leu Leu Ile Leu His Ala Asp His Glu Gln
225 230 235 240

Asn Cys Ser Thr Ser Thr Val Arg Met Ile Gly Ser Ala Gln Ala Asn
245 250 255

Met Phe Val Ser Ile Ala Gly Gly Ile Asn Ala Leu Ser Gly Pro Leu
260 265 270

His Gly Gly Ala Asn Gln Ala Val Leu Glu Met Leu Glu Asp Ile Lys
275 280 285

Asn Asn His Gly Gly Asp Ala Thr Ala Phe Met Asn Lys Val Lys Asn
290 295 300

Lys Glu Asp Gly Val Arg Leu Met Gly Phe Gly His Arg Val Tyr Lys
305 310 315 320

Asn Tyr Asp Pro Arg Ala Ala Ile Val Lys Glu Thr Ala His Glu Ile
325 330 335

Leu Glu His Leu Gly Gly Asp Asp Leu Leu Asp Leu Ala Ile Lys Leu
340 345 350

Glu Glu Ile Ala Leu Ala Asp Asp Cys Phe Ile Ser Arg Lys Leu Tyr
355 360 365

Pro Asn Val Asp Phe Tyr Thr Gly Leu Ile Tyr Arg Ala Met Gly Phe
370 375 380

Pro Thr Asp Phe Phe Thr Val Leu Phe Ala Ile Gly Arg Leu Pro Gly
385 390 395 400

Trp Ile Ala His Tyr Arg Glu Gln Leu Gly Ala Ala Gly Asn Lys Ile
405 410 415

Asn Arg Pro Arg Gln Val Tyr Thr Gly Lys Glu Ser Arg Lys Leu Val
420 425 430

Pro Arg Glu Glu Arg
435

<210> SEQ ID NO 8
<211> LENGTH: 1314
<212> TYPE: DNA
<213> ORGANISM: Corynebacterium glutamicum ATCC13869

<400> SEQUENCE: 8
atgtttgaaa gggatatcgt ggctactgat aacaacaagg ctgtcctgca ctaccccggt 60
ggcgagttcg aaatggacat catcgaggct tctgagggta acaacggtgt tgtcctgggc 120
aagatgctgt ctgagactgg actgatcact tttgacccag gttatgtgag cactggctcc 180
accgagtcga agatcaccta catcgatggc gatgcgggaa tcctgcgtta ccgcggctat 240
gacatcgctg atctggctga gaatgccacc ttcaacgagg tttcttacct acttatcaac 300
ggtgagctac caaccccaga tgagcttcac aagtttaacg acgagattcg ccaccacacc 360
cttctggacg aggacttcaa gtcccagttc aacgtgttcc cacgcgacgc tcacccaatg 420
gcaaccttgg cttcctcggt taacattttg tctacctact accaggatca gctgaaccca 480

-continued

```
ctcgatgagg cacagcttga taaggcaacc gttcgcctca tggcaaaggt tccaatgctg    540

gctgcgtacg cacaccgcgc acgcaagggt gctccttaca tgtacccaga caactccctc    600

aacgcgcgtg agaacttcct gcgcatgatg ttcggttacc caaccgagcc atacgagatc    660

gacccaatca tggtcaaggc tctggacaag ctgctcatcc tgcacgctga ccacgagcag    720

aactgctcca cctccaccgt tcgtatgatc ggttccgcac aggccaacat gtttgtctcc    780

atcgctggtg gcatcaacgc tctgtccggc ccactgcacg gtggcgcaaa ccaggctgtt    840

ctggagatgc tcgaagacat caagaacaac cacggtggcg acgcaaccgc gttcatgaac    900

aaggtcaaga acaaggaaga cggcgtccgc ctcatgggct tcggacaccg cgtttacaag    960

aactacgatc cacgtgcagc aatcgtcaag gagaccgcac acgagatcct cgagcacctc   1020

ggtggcgacg atcttctgga tctggcaatc aagctggaag aaattgcact ggctgatgat   1080

tgcttcatct cccgcaagct ctacccgaac gtagacttct acaccggcct gatctaccgc   1140

gcaatgggct tcccaactga cttcttcacc gtattgttcg caatcggtcg tctgccagga   1200

tggatcgctc actaccgcga gcagctcggt gcagcaggca acaagatcaa ccgcccacgc   1260

caggtctaca ccggcaagga atcccgcaag ttggttcctc gcgaggagcg ctaa         1314
```

```
<210> SEQ ID NO 9
<211> LENGTH: 319
<212> TYPE: PRT
<213> ORGANISM: Corynebacterium glutamicum ATCC13032

<400> SEQUENCE: 9

Met Thr Ser Gln Pro Gln Val Arg His Phe Leu Ala Asp Asp Asp Leu
1               5                   10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
    50                  55                  60

Gly Ile Ala His Leu Gly Gly His Ala Ile Val Val Asp Ser Gly Ser
65                  70                  75                  80

Ser Gln Met Gly Lys Gly Glu Ser Leu Gln Asp Thr Ala Ala Val Leu
                85                  90                  95

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
    130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
            180                 185                 190

Glu Gly Phe Gln Pro Arg Ala Glu Phe Val Glu Arg Ala Glu Lys Arg
        195                 200                 205

Gly Gln Glu Thr Gly Ala Lys Val Val Val Thr Asp Ser Leu Asp Glu
    210                 215                 220

Val Ala Gly Ala Asp Val Val Ile Thr Asp Thr Trp Val Ser Met Gly
```

-continued

```
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
    290                 295                 300

Ala Gln Lys Ala Leu Leu Val Trp Leu Leu Ala Asn Gln Pro Arg
305                 310                 315


<210> SEQ ID NO 10
<211> LENGTH: 960
<212> TYPE: DNA
<213> ORGANISM: Corynebacterium glutamicum ATCC13032

<400> SEQUENCE: 10

atgacttcac aaccacaggt tcgccatttt ctggctgatg atgatctcac ccctgcagag      60

caggcagagg ttttgaccct agccgcaaag ctcaaggcag cgccgttttc ggagcgtcca     120

ctcgagggac caaagtccgt tgcagttctt tttgataaga cttcaactcg tactcgcttc     180

tccttcgacg cgggcatcgc tcatttgggt ggacacgcca tcgtcgtgga ttccggtagc     240

tcacagatgg gtaagggcga gtccctgcag gacaccgcag ctgtattgtc ccgctacgtg     300

gaagcaattg tgtggcgcac ctacgcacac agcaatttcc acgccatggc ggagacgtcc     360

actgtgccgc tggtgaactc cttgtccgat gatctgcacc catgccagat tctggctgat     420

ctgcagacta tcgtggaaaa cctcagccct gaagaaggcc cagcaggcct taagggtaag     480

aaggctgtgt acctgggcga tggcgacaac aacatggcca actcctacat gattggcttt     540

gccaccgcgg gcatggatat ttccatcatc gctcctgaag ggttccagcc tcgtgcggaa     600

ttcgtggagc gcgcggaaaa gcgtggccag gaaaccggcg cgaaggttgt tgtcaccgac     660

agcctcgacg aggttgccgg cgccgatgtt gtcatcaccg atacctgggt atccatgggt     720

atggaaaacg acggcatcga tcgcaccaca cctttcgttc cttaccaggt caacgatgag     780

gtcatggcga aagctaacga cggcgccatc ttcctgcact gccttcctgc ctaccgtggc     840

aaagaagtgg cagcctccgt gattgatgga ccagcgtcca aagttttcga tgaagcagaa     900

aaccgcctcc acgctcagaa agcactgctg gtgtggctgc tggccaacca gccgaggtaa     960


<210> SEQ ID NO 11
<211> LENGTH: 319
<212> TYPE: PRT
<213> ORGANISM: Corynebacterium glutamicum ATCC13869

<400> SEQUENCE: 11

Met Thr Ser Gln Pro Gln Val Arg His Phe Leu Ala Asp Asp Asp Leu
1               5                   10                  15

Thr Pro Ala Glu Gln Ala Glu Val Leu Thr Leu Ala Ala Lys Leu Lys
            20                  25                  30

Ala Ala Pro Phe Ser Glu Arg Pro Leu Glu Gly Pro Lys Ser Val Ala
        35                  40                  45

Val Leu Phe Asp Lys Thr Ser Thr Arg Thr Arg Phe Ser Phe Asp Ala
    50                  55                  60

Gly Ile Ala His Leu Gly Gly His Ala Ile Val Val Asp Ser Gly Ser
65                  70                  75                  80
```

-continued

```
Ser Gln Met Gly Lys Gly Glu Thr Leu Gln Asp Thr Ala Ala Val Leu
                85                  90                  95

Ser Arg Tyr Val Glu Ala Ile Val Trp Arg Thr Tyr Ala His Ser Asn
            100                 105                 110

Phe His Ala Met Ala Glu Thr Ser Thr Val Pro Leu Val Asn Ser Leu
        115                 120                 125

Ser Asp Asp Leu His Pro Cys Gln Ile Leu Ala Asp Leu Gln Thr Ile
    130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
            180                 185                 190

Glu Gly Phe Gln Pro Arg Ala Glu Phe Val Glu Arg Ala Glu Lys Arg
        195                 200                 205

Gly Gln Glu Thr Gly Ala Lys Val Val Val Thr Asp Ser Leu Asp Glu
    210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
        275                 280                 285

Asp Gly Pro Ala Ser Lys Val Phe Asp Glu Ala Glu Asn Arg Leu His
    290                 295                 300

Ala Gln Lys Ala Leu Leu Val Trp Leu Leu Ala His Gln Pro Arg
305                 310                 315
```

<210> SEQ ID NO 12
<211> LENGTH: 960
<212> TYPE: DNA
<213> ORGANISM: Corynebacterium glutamicum ATCC13869

<400> SEQUENCE: 12

```
atgacttcac aaccacaggt tcgccatttc ctggctgatg atgatctcac ccctgcagag      60

caggcagagg ttttgaccct agccgcaaag ctcaaggcag cgccgttttc ggagcgtcca     120

ctcgagggac caaagtccgt tgcagttctt tttgataaga cttcaactcg tactcgcttc     180

tccttcgacg cgggcatcgc tcatttgggt ggacatgcca tcgtcgtgga ttccggcagc     240

tcacagatgg gtaagggcga gaccctgcag gacaccgcag ctgtattgtc ccgctacgtg     300

gaagcaattg tgtggcgcac ctacgcacac agcaatttcc acgccatggc ggagacgtcc     360

actgtgccac tggtgaactc cttgtccgat gatctgcacc catgccagat tctggctgat     420

ctgcagacca tcgtggaaaa cctcagccct gaagaaggcc cagcaggcct taagggtaag     480

aaggctgtgt acctgggcga tggcgacaac aacatggcca actcctacat gattggcttt     540

gccaccgcgg gcatggatat ctccatcatc gctcctgaag ggttccagcc tcgtgcggaa     600

ttcgtggagc gcgcggaaaa gcgtggccag gaaaccggcg cgaaggttgt tgtcaccgac     660

agcctcgacg aggttgccgg cgccgatgtt gtcatcaccg atacctgggt atccatgggt     720

atggaaaacg acggcatcga tcgcaccaca cctttcgttc cctaccaggt caacgatgag     780
```

-continued gtcatggcga aagctaacga cggcgccatc ttcctgcact gccttcctgc ctaccgcggc 840
aaagaagtgg cagcctccgt gattgatgga ccagcgtcca aagttttcga tgaagcagaa 900
aaccgcctcc acgctcagaa agcactgctg gtgtggctgc tggcccacca gccgaggtaa 960

<210> SEQ ID NO 13
<211> LENGTH: 533
<212> TYPE: PRT
<213> ORGANISM: Corynebacterium glutamicum ATCC13032

<400> SEQUENCE: 13

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Ser Glu Phe Trp Glu Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Val Ile Asn Ala Gly Asn Pro Glu Lys Glu

-continued

```
            340                 345                 350

Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Val Ser Thr Pro Ser Met Thr Val Pro Thr Thr
    450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
    530
```

<210> SEQ ID NO 14
<211> LENGTH: 1602
<212> TYPE: DNA
<213> ORGANISM: Corynebacterium glutamicum ATCC13032

<400> SEQUENCE: 14

```
atgattttag gcgtacccat tcaatatttg ctctattcat tgtggaattg gattgtcgat      60

accggttttg atgtagcaat tatcctggtc ttggcgtttt tgattccacg tatcggccga     120

ctggccatgc gtattatcaa gcgccgagtg gagtctgcag ccgatgcgga caccactaag     180

aaccagctcg cgttcgccgg cgttggcgtt tatatcgcgc aaattgtggc gtttttcatg     240

cttgccgtct ccgcgatgca ggcttttggt ttctctctcg cgggcgctgc gattccggca     300

accattgcgt cagctgccat tggccttggt gcgcagtcga ttgttgcgga cttcttggcc     360

ggatttttca tcctgacgga aaagcaattc ggcgtgggtg actgggtgcg ttttgagggc     420

aacggcatcg ttgtcgaagg caccgtcatt gagatcacca tgcgcgcgac caaaattcgc     480

acgattgcac aagagaccgt gatcatcccc aactccacgg cgaaagtgtg catcaacaat     540

tctaataact ggtcgcgtgc ggttgtcgtt attccgatcc ccatgttggg ttctgaaaac     600

atcacagatg tcatcgcgcg ctctgaagct gcgactcgtc gcgcacttgg ccaggagaaa     660

atcgcaccgg aaatcctcgg tgaactcgat gtgcacccag ccacggaagt cacgccgcca     720

acggtggtcg gcatgccgtg gatggtcacc atgcgtttcc tcgtgcaagt caccgccggc     780

aatcaatggc tggtcgaacg cgccatccgc acagaaatca tcagcgaatt ctgggaagaa     840

tacggcagcg caaccactac atcgggaacc ctcattgatt ccttacacgt tgagcatgaa     900

gagccaaaga cctcgcttat cgacgcctcc ccccaggctc ttaaggaacc gaagccggag     960

gctgcggcga cggttgcatc gctagctgca tcctctaacg acgatgcaga caatgcagac    1020
```

-continued

```
gcctcggtga tcaatgcagg caatccagag aaggaacttg attccgatgt gctggaacaa   1080

gaactctcca gcgaagaacc ggaagaaaca gcaaaaccag atcactctct ccgaggcttc   1140

ttccgcactg attactaccc aaatcggtgg cagaagatcc tgtcgtttgg cggacgtgtc   1200

cgcatgagca cgtccctgtt gttgggtgcg ctgctcttgc tgtcactatt taaggtcatg   1260

actgtggaac caagtgagaa ttggcaaaac tccagtggat ggctgtcacc aagcactgcc   1320

acctcaactg cggtgaccac ctccgaaact tccgcgccag taagcacgcc ttcgatgaca   1380

gtgcccacta cggtggagga gaccccaacg atggaatcta acgtcgaaac gcagcaggaa   1440

acctcaaccc ctgcaaccgc aacgccccag cgagccgaca ccatcgaacc gaccgaggaa   1500

gccacgtcgc aggaggaaac gactgcgtcg cagacgcagt ctccagcagt ggaagcacca   1560

accgcggtcc aagagacagt tgcgccgacg tccacccctt ag                      1602
```

<210> SEQ ID NO 15
<211> LENGTH: 533
<212> TYPE: PRT
<213> ORGANISM: Corynebacterium glutamicum ATCC13869

<400> SEQUENCE: 15

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270
```

-continued

```
Ile Ile Asn Glu Phe Trp Glu Glu Tyr Gly Ser Ala Thr Thr Thr Ser
        275                 280                 285

Gly Thr Leu Ile Asp Ser Leu His Val Glu His Glu Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Ala Ser Thr Pro Ser Met Thr Val Pro Thr Thr
    450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
        515                 520                 525

Pro Thr Ser Thr Pro
    530
```

<210> SEQ ID NO 16
<211> LENGTH: 1602
<212> TYPE: DNA
<213> ORGANISM: Corynebacterium glutamicum ATCC13869

<400> SEQUENCE: 16

```
atgattttag gcgtacccat tcaatatttg ctctattcat tgtggaattg gattgtcgat      60

accggttttg atgtagcaat tatcctggtc ttggcgtttt tgattccacg tatcggccga     120

ctggccatgc gtattatcaa gcagcgagtg gagtctgcag ccgatgcgga caccactaag     180

aaccagctcg cgttcgctgg cgttggcgtt tatatcgcgc aaattgtggc gtttttcatg     240

cttgccgtct ccgcgatgca ggcttttggt ttctctctcg cgggcgctgc gattccggca     300

accattgcgt cagctgccat tggtcttggt gcgcagtcga ttgttgcgga cttcttggcc     360

ggattttttca tcctgacgga aaagcaattc ggcgtgggtg actgggtgcg ctttgagggc     420

aacggcatcg ttgttgaagg caccgtcatt gagatcacca tgcgcgcgac caaaattcgc     480

acgattgcac aagagaccgt gatcatcccg aactccacgg cgaaagtgtg catcaacaat     540

tctaataact ggtcgcgtgc ggttgtcgtt attccgatcc ccatgttggg ttctgaaaac     600
```

```
atcacagatg tcatcgcgcg ctctgaagct gcgactcgtc gcgcacttgg ccaggagaaa    660

atcgcaccgg aaatcctcgg tgaactcgat gtgcacccag ccacggaagt cacaccgcca    720

acggtggtcg gcatgccgtg gatggtcacc atgcgtttcc tcgtgcaagt caccgccggc    780

aatcaatggc tggtcgaacg cgccatccgc acagaaatca tcaacgaatt ctgggaagaa    840

tacggcagcg caaccactac atcgggaacc ctcattgatt ccttacacgt tgagcatgaa    900

gagccaaaga cctcgcttat cgacgcctcc ccccaggctc ttaaggaacc gaagccggag    960

gctgcggcga cggttgcatc gctagctgca tcgtctaacg acgatgcaga caatgcagac   1020

gcctcggcga tcaatgcagg caatccagag aaggaacttg attccgatgt gctggaacaa   1080

gaactctcca gcgaagaacc ggaagaaaca gcaaaaccag atcactctct ccgaggcttc   1140

ttccgcactg attactaccc aaatcggtgg cagaagatcc tgtcgtttgg cggacgtgtc   1200

cgcatgagca cttccctgtt gttgggtgcg ctgctcttgc tgtcactatt taaggtcatg   1260

actgtggaac caagtgagaa ttggcaaaac tccagtggat ggctgtcacc aagcactgcc   1320

acctcaactg cggtgaccac ctccgaaact tccgcgccag caagcacgcc ttcgatgaca   1380

gtgcccacta cggtggagga gaccccaacg atggaatcta gcgtcgaaac gcagcaggaa   1440

acctcaaccc ctgcaaccgc aacgccccag cgagccgaca ccatcgaacc gaccgaggaa   1500

gccacgtcgc aggaggaaac gactgcatcg cagacgcagt ctccagcagt ggaagcacca   1560

accgcggtcc aagaaacagt tgcgccgacg tccacccctt ag                      1602
```

```
<210> SEQ ID NO 17
<211> LENGTH: 711
<212> TYPE: PRT
<213> ORGANISM: Escherichia coli

<400> SEQUENCE: 17

Met Lys Ser Met Asn Ile Ala Ala Ser Ser Glu Leu Val Ser Arg Leu
1               5                   10                  15

Ser Ser His Arg Arg Val Val Ala Leu Gly Asp Thr Asp Phe Thr Asp
            20                  25                  30

Val Ala Ala Val Val Ile Thr Ala Ala Asp Ser Arg Ser Gly Ile Leu
        35                  40                  45

Ala Leu Leu Lys Arg Thr Gly Phe His Leu Pro Val Phe Leu Tyr Ser
    50                  55                  60

Glu His Ala Val Glu Leu Pro Ala Gly Val Thr Ala Val Ile Asn Gly
65                  70                  75                  80

Asn Glu Gln Gln Trp Leu Glu Leu Glu Ser Ala Ala Cys Gln Tyr Glu
                85                  90                  95

Glu Asn Leu Leu Pro Pro Phe Tyr Asp Thr Leu Thr Gln Tyr Val Glu
            100                 105                 110

Met Gly Asn Ser Thr Phe Ala Cys Pro Gly His Gln His Gly Ala Phe
        115                 120                 125

Phe Lys Lys His Pro Ala Gly Arg His Phe Tyr Asp Phe Phe Gly Glu
    130                 135                 140

Asn Val Phe Arg Ala Asp Met Cys Asn Ala Asp Val Lys Leu Gly Asp
145                 150                 155                 160

Leu Leu Ile His Glu Gly Ser Ala Lys Asp Ala Gln Lys Phe Ala Ala
                165                 170                 175

Lys Val Phe His Ala Asp Lys Thr Tyr Phe Val Leu Asn Gly Thr Ser
            180                 185                 190
```

-continued

```
Ala Ala Asn Lys Val Val Thr Asn Ala Leu Leu Thr Arg Gly Asp Leu
        195                 200                 205

Val Leu Phe Asp Arg Asn Asn His Lys Ser Asn His His Gly Ala Leu
    210                 215                 220

Ile Gln Ala Gly Ala Thr Pro Val Tyr Leu Glu Ala Ser Arg Asn Pro
225                 230                 235                 240

Phe Gly Phe Ile Gly Gly Ile Asp Ala His Cys Phe Asn Glu Glu Tyr
                245                 250                 255

Leu Arg Gln Gln Ile Arg Asp Val Ala Pro Glu Lys Ala Asp Leu Pro
            260                 265                 270

Arg Pro Tyr Arg Leu Ala Ile Ile Gln Leu Gly Thr Tyr Asp Gly Thr
        275                 280                 285

Val Tyr Asn Ala Arg Gln Val Ile Asp Thr Val Gly His Leu Cys Asp
    290                 295                 300

Tyr Ile Leu Phe Asp Ser Ala Trp Val Gly Tyr Glu Gln Phe Ile Pro
305                 310                 315                 320

Met Met Ala Asp Ser Ser Pro Leu Leu Leu Glu Leu Asn Glu Asn Asp
                325                 330                 335

Pro Gly Ile Phe Val Thr Gln Ser Val His Lys Gln Gln Ala Gly Phe
            340                 345                 350

Ser Gln Thr Ser Gln Ile His Lys Lys Asp Asn His Ile Arg Gly Gln
        355                 360                 365

Ala Arg Phe Cys Pro His Lys Arg Leu Asn Asn Ala Phe Met Leu His
    370                 375                 380

Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
                405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
                485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
    530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
                565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
```

-continued 610 615 620

Ser Ala Tyr Ile Arg Gly Asp Val Glu Leu Val Arg Ile Arg Asp Ala
625 630 635 640

Glu Gly Arg Ile Ala Ala Glu Gly Ala Leu Pro Tyr Pro Pro Gly Val
645 650 655

Leu Cys Val Val Pro Gly Glu Val Trp Gly Gly Ala Val Gln Arg Tyr
660 665 670

Phe Leu Ala Leu Glu Glu Gly Val Asn Leu Leu Pro Gly Phe Ser Pro
675 680 685

Glu Leu Gln Gly Val Tyr Ser Glu Thr Asp Ala Asp Gly Val Lys Arg
690 695 700

Leu Tyr Gly Tyr Val Leu Lys
705 710

<210> SEQ ID NO 18
<211> LENGTH: 2136
<212> TYPE: DNA
<213> ORGANISM: Escherichia coli

<400> SEQUENCE: 18
atgaaatcaa tgaatattgc cgccagtagt gaactggtat cccgactttc ttctcatcgt 60
cgcgtggtgg cgttgggaga tactgatttt acggacgtcg cggcagtcgt cattaccgct 120
gcggatagtc gcagtggcat tcttgcgttg cttaagcgca ccggttttca tctaccggtg 180
tttttgtatt ccgaacatgc tgttgaatta cctgcgggcg ttacggcggt aatcaacggc 240
aacgagcagc agtggctgga gctggaatcc gcagcctgtc agtatgaaga gaatttgctg 300
ccaccgtttt atgacacgct gacgcagtac gttgagatgg gcaacagcac ctttgcttgc 360
cctggacatc aacatggtgc gtttttttaaa aagcatcctg ccggacgcca tttttacgat 420
ttctttggtg agaacgtctt tcgcgccgat atgtgtaacg ctgacgtaaa attgggcgat 480
ctgcttattc atgaaggatc ggcgaaagat gcgcagaaat tcgcagccaa agtctttcat 540
gccgataaaa cctattttgt gctgaacggc acatcggcag cgaataaagt ggtgacgaat 600
gcgctgttaa cgcgtggcga tctggtgctc ttcgaccgta acaaccataa gtcgaatcat 660
cacggcgcgc tgattcaggc gggggcgacg ccggtctatc tggaagcttc acgcaacccg 720
tttggtttca ttggcggtat tgatgcgcac tgttttaatg aagagtatct gcgccagcaa 780
attcgcgacg ttgcgccaga aaaagccgac ctgccgcgcc cgtatcgcct ggcgattatt 840
cagctgggaa cctatgacgg cactgtctat aacgcccgtc aggtgatcga taccgttggg 900
catctgtgtg attacattct gtttgattcc gcgtgggtcg gttatgaaca atttatcccg 960
atgatggcgg atagctcgcc gctgctgtta gaacttaacg aaaacgatcc ggggatcttt 1020
gtgactcagt cggtgcacaa acagcaggcg ggattctcac agacgtcgca gatccataaa 1080
aaagataacc atatccgcgg acaggcgcgt ttttgcccgc ataagcggtt gaataacgcc 1140
tttatgctcc atgcttctac cagccctttc tatccgctgt ttgctgcact ggatgttaac 1200
gccaaaattc atgaagggga gagtgggcgt cggctgtggg ctgagtgtgt tgagataggg 1260
attgaagcgc gcaaggctat tcttgcgcgc tgtaagctgt tccgcccgtt tatcccgccc 1320
gttgttgatg gcaaattgtg gcaggattat ccgacatcag tgttagccag cgaccgccgt 1380
tttttcagtt ttgagccggg ggcgaagtgg cacggctttg aaggatatgc cgcggatcag 1440
tattttgttg atccgtgcaa gctgttactc actacaccag gtatcgatgc cgaaaccggc 1500
gaatatagcg actttggcgt tccggcgacg attctggcgc actatctgcg tgagaacggc 1560

```
attgtgccgg agaagtgcga tctcaactcc attctgtttt tattaactcc ggcggaaagc   1620

cacgagaagc tggcacaact ggtggcgatg ctggcgcaat ttgaacagca tattgaggat   1680

gactcgccgc tggttgaggt gttgccgagc gtttataaca agtatccggt gcgctatcgc   1740

gactacaccc tgcgccagtt gtgtcaggag atgcacgatc tgtatgtcag tttcgacgtc   1800

aaagacctac aaaaagcgat gttccgccag cagagtttcc cgtcagtggt gatgaacccc   1860

caggatgcgc atagcgctta tattcgcggt gacgtggagt tggtgcggat tcgtgatgcc   1920

gaagggcgaa ttgcggcaga aggggcgttg ccttatccac ctggcgtgct ttgcgtggta   1980

cccggggaag tctggggtgg ggcggttcaa cgttatttcc ttgcactgga agaaggggtg   2040

aatttgttgc cgggatttc gccggagctg caaggtgttt atagcgaaac cgatgcggat   2100

ggcgtgaaac ggttgtacgg ttatgtgttg aagtaa                             2136


<210> SEQ ID NO 19
<211> LENGTH: 357
<212> TYPE: PRT
<213> ORGANISM: Corynebacterium glutamicum ATCC13032

<400> SEQUENCE: 19

Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
            20                  25                  30

Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
    50                  55                  60

Ile Pro Gln Leu Ala Asp Arg Val Ile Gln Asp Thr Thr Ala Glu Thr
65                  70                  75                  80

Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
        115                 120                 125

Gly Ser Glu His Gln Gly Thr Trp Pro Tyr Gly Ile Pro Glu Met Pro
    130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

Gly Leu Ile Glu Pro Asp Val Ser Val Val Ser Ile Thr Gly Val Ser
            180                 185                 190

Gly Ala Gly Lys Lys Ala Ser Val Ala Leu Leu Gly Ser Glu Thr Met
        195                 200                 205

Gly Ser Leu Lys Ala Tyr Asn Thr Ser Gly Lys His Arg His Thr Pro
    210                 215                 220

Glu Ile Ala Gln Asn Leu Gly Glu Val Ser Asp Lys Pro Val Lys Val
225                 230                 235                 240

Ser Phe Thr Pro Val Leu Ala Pro Leu Pro Arg Gly Ile Leu Thr Thr
                245                 250                 255

Ala Thr Ala Pro Leu Lys Glu Gly Val Thr Ala Glu Gln Ala Arg Ala
            260                 265                 270
```

-continued

Val Tyr Glu Glu Phe Tyr Ala Gln Glu Thr Phe Val His Val Leu Pro
275 280 285

Glu Gly Ala Gln Pro Gln Thr Gln Ala Val Leu Gly Ser Asn Met Cys
290 295 300

His Val Gln Val Glu Ile Asp Glu Glu Ala Gly Lys Val Leu Val Thr
305 310 315 320

Ser Ala Ile Asp Asn Leu Thr Lys Gly Thr Ala Gly Ala Ala Val Gln
325 330 335

Cys Met Asn Leu Ser Val Gly Phe Asp Glu Ala Ala Gly Leu Pro Gln
340 345 350

Val Gly Val Ala Pro
355

<210> SEQ ID NO 20
<211> LENGTH: 1074
<212> TYPE: DNA
<213> ORGANISM: Corynebacterium glutamicum ATCC13032

<400> SEQUENCE: 20
atgatcatgc ataacgtgta tggtgtaact atgacaatca aggttgcaat cgcaggagcc 60
agtggatatg ccggcggaga aatccttcgt ctcctttag gccatccagc ttatgcatct 120
ggtgaactag aaatcggagc actcaccgcg gcatcaaccg caggcagcac gctcggtgaa 180
ttgatgccac acattccgca gttggcggat cgtgttattc aagacaccac agctgaaact 240
ctagccggtc atgatgtcgt atttctagga cttccacacg gattctctgc agaaattgca 300
cttcagctcg gaccagatgt cacagtgatt gactgtgcag ctgactttcg tctgcaaaat 360
gctgcagatt gggagaagtt ctacggctca gagcaccagg gaacatggcc ttatggcatt 420
ccagaaatgc caggacaccg cgaggctctt cgtggtgcta agcgtgtagc agtgccagga 480
tgtttcccaa ccggtgcaac cttggctctt cttcctgcgg ttcaagcggg acttatcgag 540
ccagatgttt ccgtagtgtc catcaccggc gtatcaggtg caggtaagaa agcatctgtt 600
gcactacttg gctcggaaac catgggttca ctcaaggcgt acaacacctc cggaaagcac 660
cgccacaccc cggaaattgc ccagaacctc ggcgaagtca gcgacaagcc agtcaaggtg 720
agcttcaccc cagtgcttgc accgttacct cgcggaattc tcaccactgc aaccgcacct 780
ttgaaagaag gcgttaccgc agaacaggct cgcgcagtat atgaagagtt ctatgcacag 840
gaaaccttcg tgcatgttct tccagaaggt gcacagccac aaacccaagc agttcttggc 900
tccaacatgt gccacgtgca ggtagaaatt gatgaggaag caggcaaagt ccttgttacc 960
tccgcaatcg ataacctcac caagggaact gccggcgccg ctgttcagtg catgaactta 1020
agcgttggtt ttgatgaggc agcaggcctg ccacaggtcg gcgtcgcacc ttaa 1074

<210> SEQ ID NO 21
<211> LENGTH: 347
<212> TYPE: PRT
<213> ORGANISM: Corynebacterium glutamicum ATCC13869

<400> SEQUENCE: 21

Met Thr Ile Lys Val Ala Ile Ala Gly Ala Ser Gly Tyr Ala Gly Gly
1 5 10 15

Glu Ile Leu Arg Leu Leu Leu Gly His Pro Ala Tyr Ala Ser Gly Glu
20 25 30

Leu Glu Ile Gly Ala Leu Thr Ala Ala Ser Thr Ala Gly Ser Thr Leu
35 40 45

-continued

```
Gly Glu Leu Met Pro His Ile Pro Gln Leu Ala Asp Arg Val Ile Gln
    50                  55                  60

Asp Thr Thr Ala Glu Thr Leu Ala Gly His Asp Val Val Phe Leu Gly
65                  70                  75                  80

Leu Pro His Gly Phe Ser Ala Glu Ile Ala Leu Gln Leu Gly Pro Asp
                85                  90                  95

Val Thr Val Ile Asp Cys Ala Ala Asp Phe Arg Leu Gln Asn Ala Ala
            100                 105                 110

Asp Trp Glu Lys Phe Tyr Gly Ser Glu His Gln Gly Thr Trp Pro Tyr
        115                 120                 125

Gly Ile Pro Glu Ile Pro Gly His Arg Glu Ala Leu Arg Gly Ala Lys
    130                 135                 140

Arg Val Ala Val Pro Gly Cys Phe Pro Thr Gly Ala Thr Leu Ala Leu
145                 150                 155                 160

Leu Pro Ala Val Gln Ala Gly Leu Ile Glu Pro Asp Val Ser Val Val
                165                 170                 175

Ser Ile Thr Gly Val Ser Gly Ala Gly Lys Lys Ala Ser Val Ala Leu
            180                 185                 190

Leu Gly Ser Glu Thr Met Gly Ser Leu Lys Ala Tyr Asn Thr Ser Gly
        195                 200                 205

Lys His Arg His Thr Pro Glu Ile Ala Gln Asn Leu Gly Glu Val Ser
    210                 215                 220

Asp Lys Pro Val Lys Val Ser Phe Thr Pro Val Leu Ala Pro Leu Pro
225                 230                 235                 240

Arg Gly Ile Leu Thr Thr Ala Thr Ala Pro Leu Lys Glu Gly Val Thr
                245                 250                 255

Ala Glu Gln Ala Arg Ala Val Tyr Glu Glu Phe Tyr Ala Gln Glu Thr
            260                 265                 270

Phe Val His Val Leu Pro Glu Gly Ala Gln Pro Gln Thr Gln Ala Val
        275                 280                 285

Leu Gly Ser Asn Met Cys His Val Gln Val Glu Ile Asp Glu Glu Ala
    290                 295                 300

Gly Lys Val Leu Val Thr Ser Ala Ile Asp Asn Leu Thr Lys Gly Thr
305                 310                 315                 320

Ala Gly Ala Ala Val Gln Cys Met Asn Leu Ser Val Gly Phe Asp Glu
                325                 330                 335

Ala Ala Gly Leu Pro Gln Val Gly Val Ala Pro
            340                 345
```

<210> SEQ ID NO 22
<211> LENGTH: 1044
<212> TYPE: DNA
<213> ORGANISM: Corynebacterium glutamicum ATCC13869

<400> SEQUENCE: 22

```
atgacaatca aggttgcaat cgcaggagcc agtggatatg ccggcggaga aatccttcgt     60

ctccttttag gccatccagc ttatgcatct ggtgaactag aaatcggagc actcaccgcg    120

gcatcaaccg caggcagcac gctcggtgaa ttgatgccac acattccgca gttggcggat    180

cgtgttattc aagacaccac agctgaaact ctagccggtc atgatgtcgt atttctagga    240

cttccacacg gattctctgc agaaattgca cttcagctcg gaccagatgt cacagtgatt    300

gactgtgcag ctgactttcg tctgcaaaat gctgcagatt gggagaagtt ctacggctca    360

gagcaccagg gaacatggcc ttatggcatt ccagaaatac caggacaccg cgaggctctt    420
```

```
cgtggtgcta agcgtgtagc agtgccagga tgtttcccaa ccggtgcaac cttggctctt    480

cttcctgcgg ttcaagcggg acttatcgag ccagatgttt ccgtagtgtc catcaccggc    540

gtatcaggtg caggtaagaa agcatctgtt gcactacttg gctcggaaac catgggttca    600

ctcaaggcgt acaacacctc cggaaagcac cgccacaccc cggaaattgc ccagaacctc    660

ggcgaagtca gcgacaagcc agtcaaggtg agcttcaccc cagtgcttgc accgttacct    720

cgcggaattc tcaccactgc aaccgcacct ttgaaagaag gcgttaccgc agagcaggct    780

cgcgcagtat atgaagagtt ctatgcacag gaaaccttcg tgcatgttct tccagaaggt    840

gcacagccac aaacccaagc agttcttggc tccaacatgt gccacgtgca ggtagaaatt    900

gatgaggaag caggcaaagt ccttgttacc tccgcaatcg ataacctcac caagggaact    960

gccggcgccg ctgttcagtg catgaactta agcgttggct ttgatgaggc agcaggcctg   1020

ccacaggtcg gcgtcgcacc ttaa                                          1044


<210> SEQ ID NO 23
<211> LENGTH: 388
<212> TYPE: PRT
<213> ORGANISM: Corynebacterium glutamicum ATCC13032

<400> SEQUENCE: 23

Met Ala Glu Lys Gly Ile Thr Ala Pro Lys Gly Phe Val Ala Ser Ala
1               5                   10                  15

Thr Thr Ala Gly Ile Lys Ala Ser Gly Asn Pro Asp Met Ala Leu Val
            20                  25                  30

Val Asn Gln Gly Pro Glu Phe Ser Ala Ala Ala Val Phe Thr Arg Asn
        35                  40                  45

Arg Val Phe Ala Ala Pro Val Lys Val Ser Arg Glu Asn Val Ala Asp
    50                  55                  60

Gly Gln Ile Arg Ala Val Leu Tyr Asn Ala Gly Asn Ala Asn Ala Cys
65                  70                  75                  80

Asn Gly Leu Gln Gly Glu Lys Asp Ala Arg Glu Ser Val Ser His Leu
                85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Ala Gly Ile
        115                 120                 125

Asp Gln Leu Thr Ala Glu Gly Ala Leu Gly Asp Asn Gly Ala Ala Ala
    130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
        195                 200                 205

Val Thr Phe Asp Thr Leu Asp Ile Asp Gly Ser Thr Ser Thr Asn Asp
    210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255
```

```
Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
        275                 280                 285

Val Ala Arg Asp Asn Leu Phe Lys Cys Ala Met Phe Gly Ser Asp Pro
    290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365

Thr Val Arg Thr Thr Asp Leu Ser Phe Ser Tyr Val Glu Ile Asn Ser
    370                 375                 380

Ala Tyr Ser Ser
385
```

<210> SEQ ID NO 24
<211> LENGTH: 1167
<212> TYPE: DNA
<213> ORGANISM: Corynebacterium glutamicum ATCC13032

<400> SEQUENCE: 24

```
atggcagaaa aaggcattac cgcgccgaaa ggcttcgttg cttctgcaac gaccgcgggt     60

attaaagctt ctggcaatcc tgacatggcg ttggtggtta accagggtcc agagttttcc    120

gcagcggccg tgtttacacg taaccgagtt ttcgcagcgc ctgtgaaggt gagccgagag    180

aacgttgctg atggccagat cagggctgtt ttgtacaacg ctggtaatgc taatgcgtgt    240

aatggtctgc agggtgagaa ggatgctcgt gagtctgttt ctcatctagc tcaaaatttg    300

ggcttggagg attccgatat tggtgtgtgt tccactggtc ttattggtga gttgcttccg    360

atggataagc tcaatgcagg tattgatcag ctgaccgctg agggcgcttt gggtgacaat    420

ggtgcagctg ctgccaaggc gatcatgacc actgacacgg tggataagga aaccgtcgtg    480

tttgctgatg gttggactgt cggcggaatg ggcaagggcg tgggcatgat ggcgccgtct    540

cttgccacca tgctggtctg cttgaccact gatgcatccg ttactcagga aatggctcag    600

atcgcgctgg ctaatgctac ggccgttacg tttgacaccc tggatattga tggatcaacc    660

tccaccaatg acaccgtgtt cctgctggca tctggcgcta gcggaatcac cccaactcag    720

gatgaactca acgatgcggt gtacgcagct tgttctgata tcgcagcgaa gcttcaggct    780

gatgcagagg gtgtgaccaa gcgcgttgct gtgacagtgg tgggaaccac caacaacgag    840

caggcgatta atgcggctcg cactgttgct cgtgacaatt tgttcaagtg cgcaatgttt    900

ggatctgatc caaactgggg tcgcgtgttg gctgcagtcg gcatggctga tgctgatatg    960

gaaccagaga agatttctgt gttcttcaat ggtcaagcag tatgccttga ttccactggc   1020

gctcctggtg ctcgtgaggt ggatctttcc ggcgctgaca ttgatgtccg aattgatttg   1080

ggcaccagtg gggaaggcca ggcaacagtt cgaaccactg acctgagctt ctcctacgtg   1140

gagatcaact ccgcgtacag ctcttaa                                       1167
```

<210> SEQ ID NO 25
<211> LENGTH: 388
<212> TYPE: PRT

-continued

<213> ORGANISM: Corynebacterium glutamicum ATCC13869

<400> SEQUENCE: 25

Met Ala Lys Lys Gly Ile Thr Ala Pro Lys Gly Phe Val Ala Ser Ala
1               5                   10                  15

Thr Thr Ala Gly Ile Lys Ala Ser Gly Asn Pro Asp Met Ala Leu Val
            20                  25                  30

Val Asn Gln Gly Pro Glu Phe Ser Ala Ala Ala Val Phe Thr Arg Asn
        35                  40                  45

Arg Val Phe Ala Ala Pro Val Lys Val Ser Arg Glu Asn Val Ala Asp
    50                  55                  60

Gly Gln Ile Arg Ala Val Leu Tyr Asn Ala Gly Asn Ala Asn Ala Cys
65                  70                  75                  80

Asn Gly Leu Gln Gly Glu Lys Asp Ala Arg Glu Ser Val Ser His Leu
                85                  90                  95

Ala Gln Asn Leu Gly Leu Glu Asp Ser Asp Ile Gly Val Cys Ser Thr
            100                 105                 110

Gly Leu Ile Gly Glu Leu Leu Pro Met Asp Lys Leu Asn Thr Gly Ile
        115                 120                 125

Asp Gln Leu Thr Ala Glu Gly Ala Leu Gly Asp Asn Gly Ala Ala Ala
    130                 135                 140

Ala Lys Ala Ile Met Thr Thr Asp Thr Val Asp Lys Glu Thr Val Val
145                 150                 155                 160

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
            180                 185                 190

Ser Val Thr Gln Glu Met Ala Gln Ile Ala Leu Ala Asn Ala Thr Ala
        195                 200                 205

Val Thr Phe Asp Thr Leu Asp Ile Asp Gly Ser Thr Ser Thr Asn Asp
    210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
            260                 265                 270

Val Val Gly Thr Thr Asn Asn Glu Gln Ala Ile Asn Ala Ala Arg Thr
        275                 280                 285

Val Ala Arg Asp Asn Leu Phe Lys Cys Ala Met Phe Gly Ser Asp Pro
    290                 295                 300

Asn Trp Gly Arg Val Leu Ala Ala Val Gly Met Ala Asp Ala Asp Met
305                 310                 315                 320

Glu Pro Glu Lys Ile Ser Val Phe Phe Asn Asp Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
        355                 360                 365

Thr Val Arg Thr Thr Asp Leu Ser Phe Ser Tyr Val Glu Ile Asn Ser
    370                 375                 380

Ala Tyr Ser Ser
385

<210> SEQ ID NO 26
<211> LENGTH: 1167
<212> TYPE: DNA
<213> ORGANISM: Corynebacterium glutamicum ATCC13869

<400> SEQUENCE: 26
atggccaaaa aaggcattac cgcgccgaaa ggcttcgttg cttctgcaac gaccgcgggt 60
attaaagctt ctggcaatcc tgacatggcg ttggtggtta accagggtcc agagttttcc 120
gcagcggccg tgtttacacg caaccgagtt ttcgcagcgc ctgtgaaggt gagccgggag 180
aacgttgctg atggccagat cagggctgtt ttgtacaacg ctggtaatgc taatgcgtgt 240
aatggtctgc agggtgagaa ggatgctcgt gagtctgttt ctcatctagc tcaaaatttg 300
ggcttggagg attccgatat tggtgtgtgt tccactggtc ttattggtga gttgcttccg 360
atggataagc tcaatacagg tattgatcag ctgaccgctg agggcgcttt gggtgacaat 420
ggtgcagctg ctgccaaggc gatcatgacc actgacacgg tggataagga aaccgtcgtg 480
tttgctgatg gttggactgt cggcggaatg ggcaagggcg tgggcatgat ggcgccgtct 540
cttgccacca tgctggtctg cttgaccact gatgcatccg ttactcagga aatggctcag 600
attgcgctgg ctaatgctac ggccgttacg tttgacaccc tggatattga tggatcaacc 660
tccaccaatg acaccgtgtt cctgctggca tctggcgcta gcggaatcac cccaactcag 720
gatgaactca acgatgcggt gtacgcagct tgttctgata tcgcagcgaa gcttcaggct 780
gatgcagagg gggtgaccaa gcgcgttgct gtgacagtgg tgggaaccac caacaacgag 840
caggcgatca atgcggctcg cacggttgct cgtgacaatt tgttcaagtg cgcaatgttt 900
ggatctgatc caaactgggg tcgcgtgttg gctgcagtcg gcatggctga tgctgatatg 960
gaaccagaga agatttctgt gttcttcaat gatcaagcag tatgccttga ttccactggc 1020
gctcctggtg ctcgtgaggt ggatctttcc ggcgctgaca ttgatgtccg aattgatttg 1080
ggcaccagtg gggaaggcca ggcaacagtt cgaaccactg acctgagctt ctcctacgtg 1140
gagatcaact ccgcgtacag ctcttaa 1167

<210> SEQ ID NO 27
<211> LENGTH: 317
<212> TYPE: PRT
<213> ORGANISM: Corynebacterium glutamicum ATCC13032

<400> SEQUENCE: 27

Met Asn Asp Leu Ile Lys Asp Leu Gly Ser Glu Val Arg Ala Asn Val
1 5 10 15

Leu Ala Glu Ala Leu Pro Trp Leu Gln His Phe Arg Asp Lys Ile Val
20 25 30

Val Val Lys Tyr Gly Gly Asn Ala Met Val Asp Asp Asp Leu Lys Ala
35 40 45

Ala Phe Ala Ala Asp Met Val Phe Leu Arg Thr Val Gly Ala Lys Pro
50 55 60

Val Val Val His Gly Gly Gly Pro Gln Ile Ser Glu Met Leu Asn Arg
65 70 75 80

Val Gly Leu Gln Gly Glu Phe Lys Gly Gly Phe Arg Val Thr Thr Pro
85 90 95

Glu Val Met Asp Ile Val Arg Met Val Leu Phe Gly Gln Val Gly Arg
100 105 110

Asp Leu Val Gly Leu Ile Asn Ser His Gly Pro Tyr Ala Val Gly Thr
115 120 125

```
Ser Gly Glu Asp Ala Gly Leu Phe Thr Ala Gln Lys Arg Met Val Asn
    130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ala Ile Gly Ala Glu
        195                 200                 205

Arg Leu Leu Val Leu Thr Asn Val Glu Gly Leu Tyr Thr Asp Trp Pro
    210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
    290                 295                 300

Gly Thr Val Phe Arg Lys Asp Asp Lys Asp Gly Glu Leu
305                 310                 315


<210> SEQ ID NO 28
<211> LENGTH: 954
<212> TYPE: DNA
<213> ORGANISM: Corynebacterium glutamicum ATCC13032

<400> SEQUENCE: 28

atgaatgact tgatcaaaga tttaggctct gaggtgcgcg caaatgtcct cgctgaggcg      60

ttgccatggt tgcagcactt ccgcgacaag attgttgtcg tgaaatatgg cggaaacgcc     120

atggtggatg atgatctcaa ggctgctttt gctgccgaca tggtcttctt gcgcaccgtg     180

ggcgcaaaac cagtggtggt gcacggtggt ggacctcaga tttctgagat gctaaaccgt     240

gtgggtctcc agggcgagtt caagggtggt ttccgtgtga ccactcctga ggtcatggac     300

attgtgcgca tggtgctctt tggtcaggtc ggtcgcgatt tagttggttt gatcaactct     360

catggccctt acgctgtggg aacctccggt gaggatgccg gcctgtttac cgcgcagaag     420

cgcatggtca acatcgatgg cgtacccact gatattggtt tggtcggaga catcattaat     480

gtcgatgcct cttccttgat ggatatcatc gaggccggtc gcattcctgt ggtctctacg     540

attgctccag gcgaagacgg ccagatttac aacattaacg ccgataccgc agcaggtgct     600

ttggctgcag cgattggtgc agaacgcctg ctggttctca ccaatgtgga aggtctgtac     660

accgattggc ctgataagag ctcactggtg tccaagatca aggccaccga gctggaggcc     720

attcttccgg gacttgattc cggcatgatt ccaaagatgg agtcttgctt gaacgcggtg     780

cgtgggggag taagcgctgc tcatgtcatt gacggccgca tcgcgcactc ggtgttgctg     840

gagcttttga ccatgggtgg aattggcacg atggtgctgc cggatgtttt tgatcgggag     900

aattatcctg aaggcaccgt ttttagaaaa gacgacaagg atggggaact gtaa          954


<210> SEQ ID NO 29
```

-continued

<211> LENGTH: 317
<212> TYPE: PRT
<213> ORGANISM: Corynebacterium glutamicum ATCC13869

<400> SEQUENCE: 29

```
Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
            20                  25                  30

Val Val Lys Tyr Gly Gly Asn Ala Met Val Asp Asp Asp Leu Lys Ala
        35                  40                  45

Ala Phe Ala Ala Asp Met Val Phe Leu Arg Thr Val Gly Ala Lys Pro
    50                  55                  60

Val Val Val His Gly Gly Gly Pro Gln Ile Ser Glu Met Leu Asn Arg
65                  70                  75                  80

Val Gly Leu Gln Gly Glu Phe Lys Gly Gly Phe Arg Val Thr Thr Pro
                85                  90                  95

Glu Val Met Asp Ile Val Arg Met Val Leu Phe Gly Gln Val Gly Arg
            100                 105                 110

Asp Leu Val Gly Leu Ile Asn Ser His Gly Pro Tyr Ala Val Gly Thr
        115                 120                 125

Ser Gly Glu Asp Ala Gly Leu Phe Thr Ala Gln Lys Arg Met Val Asn
    130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ala Ile Gly Ala Glu
        195                 200                 205

Arg Leu Leu Val Leu Thr Asn Val Glu Gly Leu Tyr Thr Asp Trp Pro
    210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
    290                 295                 300

Gly Thr Val Phe Arg Lys Asp Asp Lys Asp Gly Glu Leu
305                 310                 315
```

<210> SEQ ID NO 30
<211> LENGTH: 954
<212> TYPE: DNA
<213> ORGANISM: Corynebacterium glutamicum ATCC13869

<400> SEQUENCE: 30

```
atgaatgact tgatcaaaga tttaggctct gaggtgcgcg caaatgtcct cgctgaggcg      60

ttgccatggt tgcagcattt ccgcgacaag attgttgtcg tgaaatatgg cggaaacgcc     120

atggtggatg atgatctcaa ggctgctttt gctgccgaca tggtcttctt gcgcaccgtg     180
```

-continued

```
ggcgcaaaac cagtggtggt gcacggtggt ggacctcaga tttctgagat gctaaaccgt    240

gtgggtctcc agggcgagtt caagggtggt ttccgtgtga ccactcctga ggtcatggac    300

attgtgcgca tggtgctctt tggtcaggtc ggtcgcgatt tagttggttt gatcaactct    360

catggccctt acgctgtggg aacctccggt gaggatgccg gcctgtttac cgcgcagaag    420

cgcatggtca acatcgatgg cgtacccact gatattggtt tggtcggaga catcattaat    480

gtcgatgcct cttccttgat ggatatcatc gaggccggtc gcattcctgt ggtctctacg    540

attgctccag gcgaagacgg ccagatttac aacatcaacg ccgataccgc agcgggtgct    600

ttggctgcag cgattggtgc agaacgcctg ctggttctca ccaatgtgga aggtctgtac    660

accgattggc ctgataagag ctcactggtg tccaagatca aggccaccga gctggaggcc    720

attcttccgg gacttgattc cggcatgatt ccaaagatgg agtcttgctt gaatgcggtg    780

cgtgggggag taagcgctgc tcatgtcatt gacggccgca tcgcgcactc ggtgttgctg    840

gagcttttga ccatgggtgg aattggcacg atggtgctgc cggatgtttt tgatcgggag    900

aattatccgg aaggcaccgt tttagaaaa gacgacaagg atggggaact gtaa          954
```

<210> SEQ ID NO 31
<211> LENGTH: 391
<212> TYPE: PRT
<213> ORGANISM: Corynebacterium glutamicum ATCC13032

<400> SEQUENCE: 31

```
Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
            20                  25                  30

Asp Gln Gly Asn Val Tyr Ile Asp Leu Leu Ala Gly Ile Ala Val Asn
        35                  40                  45

Ala Leu Gly His Ala His Pro Ala Ile Ile Glu Ala Val Thr Asn Gln
    50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
    130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
    210                 215                 220

Glu Val Gln Thr Gly Val Gly Arg Thr Gly Asp Phe Phe Ala His Gln
225                 230                 235                 240
```

-continued

His Asp Gly Val Val Pro Asp Val Val Thr Met Ala Lys Gly Leu Gly
245 250 255

Gly Gly Leu Pro Ile Gly Ala Cys Leu Ala Thr Gly Arg Ala Ala Glu
260 265 270

Leu Met Thr Pro Gly Lys His Gly Thr Thr Phe Gly Gly Asn Pro Val
275 280 285

Ala Cys Ala Ala Ala Lys Ala Val Leu Ser Val Val Asp Asp Ala Phe
290 295 300

Cys Ala Glu Val Ala Arg Lys Gly Glu Leu Phe Lys Glu Leu Leu Ala
305 310 315 320

Lys Val Asp Gly Val Val Asp Val Arg Gly Arg Gly Leu Met Leu Gly
325 330 335

Val Val Leu Glu Arg Asp Val Ala Lys Gln Ala Val Leu Asp Gly Phe
340 345 350

Lys His Gly Val Ile Leu Asn Ala Pro Ala Asp Asn Ile Ile Arg Leu
355 360 365

Thr Pro Pro Leu Val Ile Thr Asp Glu Glu Ile Ala Asp Ala Val Lys
370 375 380

Ala Ile Ala Glu Thr Ile Ala
385 390

<210> SEQ ID NO 32
<211> LENGTH: 1176
<212> TYPE: DNA
<213> ORGANISM: Corynebacterium glutamicum ATCC13032

<400> SEQUENCE: 32
atgagcacgc tggaaacttg gccacaggtc attattaata cgtacggcac cccaccagtt 60
gagctggtgt ccggcaaggg cgcaaccgtc actgatgacc agggcaatgt ctacatcgac 120
ttgctcgcgg gcatcgcagt caacgcgttg ggccacgccc acccggcgat catcgaggcg 180
gtcaccaacc agatcggcca acttggtcac gtctcaaact tgttcgcatc caggcccgtc 240
gtcgaggtcg ccgaggagct catcaagcgt ttttcgcttg acgacgccac cctcgccgcg 300
caaacccggg ttttcttctg caactcgggc gccgaagcaa acgaggctgc tttcaagatt 360
gcacgcttga ctggtcgttc ccggattctg gctgcagttc atggtttcca cggccgcacc 420
atgggttccc tcgcgctgac tggccagcca gacaagcgtg aagcgttcct gccaatgcca 480
agcggtgtgg agttctaccc ttacggcgac accgattact tgcgcaaaat ggtagaaacc 540
aacccaacgg atgtggctgc tatcttcctc gagccaatcc agggtgaaac gggcgttgtt 600
ccagcacctg aaggattcct caaggcagtg cgcgagctgt gcgatgagta cggcatcttg 660
atgatcaccg atgaagtcca gactggcgtt ggccgtaccg gcgatttctt tgcacatcag 720
cacgatggcg ttgttcccga tgtggtgacc atggccaagg gacttggcgg cggtcttccc 780
atcggtgctt gtttggccac tggccgtgca gctgaattga tgaccccagg caagcacggc 840
accactttcg gtggcaaccc agttgcttgt gcagctgcca aggcagtgct gtctgttgtc 900
gatgacgctt tctgcgcaga agttgcccgc aagggcgagc tgttcaagga acttcttgcc 960
aaggttgacg gcgttgtaga cgtccgtggc aggggcttga tgttgggcgt ggtgctggag 1020
cgcgacgtcg caaagcaagc tgttcttgat ggttttaagc acggcgttat tttgaatgca 1080
ccggcggaca acattatccg tttgaccccg ccgctggtga tcaccgacga agaaatcgca 1140
gacgcagtca aggctattgc cgagacaatc gcataa 1176

-continued

```
<210> SEQ ID NO 33
<211> LENGTH: 391
<212> TYPE: PRT
<213> ORGANISM: Corynebacterium glutamicum ATCC13869

<400> SEQUENCE: 33

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
            20                  25                  30

Asp Gln Gly Lys Val Tyr Ile Asp Leu Leu Ala Gly Ile Ala Val Asn
        35                  40                  45

Ala Leu Gly His Ala His Pro Ala Ile Ile Glu Ala Val Thr Asn Gln
    50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
    130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
    210                 215                 220

Glu Val Gln Thr Gly Val Gly Arg Thr Gly Asp Phe Phe Ala His Gln
225                 230                 235                 240

His Asp Gly Val Val Pro Asp Val Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
        275                 280                 285

Ala Cys Ala Ala Ala Lys Ala Val Leu Ser Val Val Asp Asp Ala Phe
    290                 295                 300

Cys Ala Glu Val Thr Arg Lys Gly Glu Leu Phe Lys Glu Leu Leu Ala
305                 310                 315                 320

Lys Val Asp Gly Val Val Asp Val Arg Gly Arg Gly Leu Met Leu Gly
                325                 330                 335

Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
    370                 375                 380
```

Ala Ile Ala Glu Thr Ile Ala
385 390

<210> SEQ ID NO 34
<211> LENGTH: 1176
<212> TYPE: DNA
<213> ORGANISM: Corynebacterium glutamicum ATCC13869

<400> SEQUENCE: 34
atgagcacgc tggaaacttg gccacaggtc attattaata cgtacggcac cccaccagtt 60
gagctggtgt ccggcaaggg cgcaaccgtc accgatgacc agggcaaagt ctacatcgac 120
ttgctcgcgg gcatcgcagt caacgcgttg ggccacgccc acccggcgat catcgaggcg 180
gtcaccaacc agatcggcca acttggtcac gtctcaaact tgttcgcatc caggcccgtc 240
gtcgaggtcg ccgaggagct catcaagcgt ttttcgcttg acgacgccac cctcgccgcg 300
caaacccggg ttttcttctg caactcgggc gccgaagcaa acgaggctgc tttcaagatt 360
gcacgcttga ctggtcgttc ccggattctg gctgcagttc atggtttcca cggccgcacc 420
atgggttccc tcgcgctgac tggccagcca gacaagcgtg aagcattcct gccaatgcca 480
agcggtgtgg agttctaccc ttacggcgac accgattact tgcgcaaaat ggtagaaacc 540
aacccaacgg atgtggctgc tatcttcctc gagccaatcc agggtgaaac gggcgttgtt 600
ccagcacctg aaggattcct caaggcagtg cgcgagctgt gcgatgagta cggcatcttg 660
atgatcaccg atgaagtcca gactggcgtt ggccgtaccg gcgatttctt tgcacatcag 720
cacgatggcg ttgttcccga tgtggtgacc atggccaagg gacttggcgg cggtcttccc 780
atcggtgctt gtttggccac tggccgtgca gctgaattga tgaccccagg caagcacggc 840
accactttcg gtggcaaccc agttgcttgt gcagctgcca aggcagtgct gtctgttgtc 900
gatgacgctt tctgcgcaga agttacccgc aagggcgagc tgttcaagga acttcttgcc 960
aaggttgacg gcgttgtaga cgtccgtggc aggggcttga tgttgggcgt ggtgctggag 1020
cgcgacgtcg caaagcaagc tgttcttgat ggttttaagc acggcgttat tttgaatgca 1080
ccggcggaca acattatccg tttgaccccg ccgctggtga tcaccgacga agaaatcgca 1140
gacgcagtca aggctattgc cgagacaatc gcataa 1176

<210> SEQ ID NO 35
<211> LENGTH: 203
<212> TYPE: PRT
<213> ORGANISM: Corynebacterium glutamicum ATCC13032

<400> SEQUENCE: 35

Met Ser Pro Thr Val Leu Pro Ala Thr Gln Ala Asp Phe Pro Lys Ile
1 5 10 15

Val Asp Val Leu Val Glu Ala Phe Ala Asn Asp Pro Ala Phe Leu Arg
20 25 30

Trp Ile Pro Gln Pro Asp Pro Gly Ser Ala Lys Leu Arg Ala Leu Phe
35 40 45

Glu Leu Gln Ile Glu Lys Gln Tyr Ala Val Ala Gly Asn Ile Asp Val
50 55 60

Ala Arg Asp Ser Glu Gly Glu Ile Val Gly Val Ala Leu Trp Asp Arg
65 70 75 80

Pro Asp Gly Asn His Ser Ala Lys Asp Gln Ala Ala Met Leu Pro Arg
85 90 95

Leu Val Ser Ile Phe Gly Ile Lys Ala Ala Gln Val Ala Trp Thr Asp

-continued 100 105 110

Leu Ser Ser Ala Arg Phe His Pro Lys Phe Pro His Trp Tyr Leu Tyr
115 120 125

Thr Val Ala Thr Ser Ser Ser Ala Arg Gly Thr Gly Val Gly Ser Ala
130 135 140

Leu Leu Asn His Gly Ile Ala Arg Ala Gly Asp Glu Ala Ile Tyr Leu
145 150 155 160

Glu Ala Thr Ser Thr Arg Ala Ala Gln Leu Tyr Asn Arg Leu Gly Phe
165 170 175

Val Pro Leu Gly Tyr Ile Pro Ser Asp Asp Asp Gly Thr Pro Glu Leu
180 185 190

Ala Met Trp Lys Pro Pro Ala Met Pro Thr Val
195 200

<210> SEQ ID NO 36
<211> LENGTH: 612
<212> TYPE: DNA
<213> ORGANISM: Corynebacterium glutamicum ATCC13032

<400> SEQUENCE: 36
atgagtccca ccgttttgcc tgctacacaa gctgacttcc ctaagatcgt cgatgttctg 60
gttgaagcat tcgccaacga tccagcattt ttacgatgga tcccgcagcc ggaccccggt 120
tcagcaaagc ttcgagcact tttcgaactg cagattgaga agcagtatgc agtggcggga 180
aatattgatg tcgcgcgtga ttctgaggga gaaatcgtcg gcgtcgcgtt atgggatcgg 240
ccagatggta atcacagtgc caaagatcaa gcagcgatgc tcccccggct cgtctccatt 300
ttcgggatca aggctgcgca ggtggcgtgg acggatttga gttcggctcg tttccacccc 360
aaattccccc attggtacct ctacaccgtg gcaacatcta gttctgcccg tggaacgggt 420
gttggcagtg cgcttcttaa tcacggaatc gctcgcgcgg gtgatgaagc tatctatttg 480
gaggcgacgt cgactcgtgc ggctcaacta tataaccgtc tgggatttgt gcccttgggt 540
tatatcccct cagatgatga tggcactcct gaactggcga tgtggaaacc gccagcgatg 600
ccaactgttt aa 612

<210> SEQ ID NO 37
<211> LENGTH: 203
<212> TYPE: PRT
<213> ORGANISM: Corynebacterium glutamicum ATCC13869

<400> SEQUENCE: 37

Met Ser Pro Thr Val Leu Pro Ala Thr Gln Ala Asp Phe Pro Lys Ile
1 5 10 15

Val Asp Val Leu Val Glu Ala Phe Ala Asn Asp Pro Ala Phe Leu Arg
20 25 30

Trp Ile Pro Gln Pro Asp Pro Gly Ser Ala Lys Leu Arg Ala Leu Phe
35 40 45

Glu Leu Gln Ile Glu Lys Gln Tyr Ala Val Ala Gly Asn Ile Asp Val
50 55 60

Ala Arg Asp Ser Glu Gly Glu Ile Val Gly Val Ala Leu Trp Asp Arg
65 70 75 80

Pro Asp Gly Asn His Ser Ala Lys Asp Gln Ala Ala Ile Leu Pro Arg
85 90 95

Leu Val Ser Ile Phe Gly Ile Lys Ala Ala Gln Val Ala Trp Thr Asp
100 105 110

```
Leu Ser Ser Ala Arg Phe His Pro Lys Phe Pro His Trp Tyr Leu Tyr
        115                 120                 125

Thr Val Ala Thr Ser Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                165                 170                 175

Val Pro Leu Gly Tyr Ile Pro Ser Asp Asp Asp Gly Thr Pro Glu Leu
            180                 185                 190

Ala Met Trp Lys Pro Pro Ala Met Pro Thr Val
        195                 200


<210> SEQ ID NO 38
<211> LENGTH: 612
<212> TYPE: DNA
<213> ORGANISM: Corynebacterium glutamicum ATCC13869

<400> SEQUENCE: 38

atgagtccca ccgttttgcc tgctacacaa gctgacttcc ctaagatcgt cgatgttctg      60

gttgaagcat tcgccaacga tccagcattt ttacgatgga tcccgcagcc ggaccccggt     120

tcagcaaagc ttcgagcact tttcgaactg cagattgaga agcagtatgc agtggcggga     180

aatattgatg tcgcgcgtga ttctgaggga gaaatcgtcg gcgtcgcgtt atgggatcgg     240

ccagatggta atcacagtgc caaagatcaa gcagcgatac tcccccggct cgtctccatt     300

ttcgggatca aggctgcgca ggtggcgtgg acggatttga gttcggctcg tttccacccc     360

aaattccccc attggtacct ctacaccgtg gcaacatcta gttctgcccg tggaacgggt     420

gttggcagtg cgcttcttaa tcacggaatc gctcgcgcgg gtgatgaagc tatctatttg     480

gaggcgacgt cgactcgtgc ggctcaacta tataaccgtc tgggatttgt gcccttgggt     540

tatatcccct cagatgatga tggcactcct gaactggcga tgtggaaacc gccagcgatg     600

ccaactgttt aa                                                         612


<210> SEQ ID NO 39
<211> LENGTH: 494
<212> TYPE: PRT
<213> ORGANISM: Corynebacterium glutamicum ATCC13032

<400> SEQUENCE: 39

Met Thr Ser Glu Thr Leu Gln Ala Gln Ala Pro Thr Lys Thr Gln Arg
1               5                   10                  15

Trp Ala Phe Leu Ala Val Ile Ser Gly Gly Leu Phe Leu Ile Gly Val
            20                  25                  30

Asp Asn Ser Ile Leu Tyr Thr Ala Leu Pro Leu Leu Arg Glu Gln Leu
        35                  40                  45

Ala Ala Thr Glu Thr Gln Ala Leu Trp Ile Ile Asn Ala Tyr Pro Leu
    50                  55                  60

Leu Met Ala Gly Leu Leu Leu Gly Thr Gly Thr Leu Gly Asp Lys Ile
65                  70                  75                  80

Gly His Arg Arg Met Phe Leu Met Gly Leu Ser Ile Phe Gly Ile Ala
                85                  90                  95

Ser Leu Gly Ala Ala Phe Ala Pro Thr Ala Trp Ala Leu Val Ala Ala
            100                 105                 110

Arg Ala Phe Leu Gly Ile Gly Ala Ala Thr Met Met Pro Ala Thr Leu
        115                 120                 125
```

```
Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Ile Thr Ile
    210                 215                 220

Lys Glu Ser Val Asn Thr Ala Arg His Met Pro Leu Leu Leu Gly Ala
225                 230                 235                 240

Val Ile Met Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Ala Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Asp Gly Asp Ala Ala Arg Ala Ser Leu Asp Thr Ala Tyr Ile Asn Val
    450                 455                 460

Leu Ile Ile Ala Leu Val Cys Ala Val Ala Ala Ala Leu Ile Ser Ser
465                 470                 475                 480

Tyr Leu Phe Arg Gly Asn Pro Lys Gly Ala Asn Asn Ala His
                485                 490
```

<210> SEQ ID NO 40
<211> LENGTH: 1485
<212> TYPE: DNA
<213> ORGANISM: Corynebacterium glutamicum ATCC13032

<400> SEQUENCE: 40

```
atgacttcag aaaccttaca ggcgcaagcg cctacgaaaa cccaacgttg ggctttcctc      60
```

gccgttatca gcggtggtct ctttctgatc ggtgtagaca actcgattct ctacaccgca 120
ctccctctgc tgcgtgaaca gctcgcagcc accgaaaccc aagcgttgtg gatcatcaac 180
gcatatcccc tgctcatggc gggccttctt ttgggtaccg gcactttggg tgacaaaatc 240
ggccaccgcc ggatgttcct catgggcttg agcattttcg gaatcgcttc acttggtgct 300
gcgtttgctc caactgcgtg ggctcttgtt gctgcgagag ctttccttgg catcggtgcg 360
gcaacgatga tgcctgcaac cttggctctg atccgcatta cgtttgagga tgagcgtgag 420
cgcaacactg caattggtat ttggggttcc gtggcaattc ttggcgctgc ggcaggcccg 480
atcattggtg gtgcgctgtt ggaattcttc tggtggggtt cggttttcct cattaacgtt 540
ccggtggctg ttatcgcgtt gatcgctacg ctttttgtgg cgccggccaa tatcgcgaat 600
ccgtctaagc attgggattt cttgtcgtcg ttctatgcgc tgctcacact tgctgggttg 660
atcatcacga tcaaggaatc tgtgaatact gcacgccata tgcctcttct tttgggtgca 720
gtcatcatgt tgatcattgg tgcggtgttg tttagcagtc gtcagaagaa gatcgaggag 780
ccacttctag atctgtcgtt gttccgtaat cgccttttct taggcggtgt ggttgctgcg 840
ggcatggcga tgtttactgt gtccggtttg gaaatgacta cctcgcagcg tttccagttg 900
tctgtgggtt tcactccact tgaggctggt ttgctcatga tcccagctgc attgggtagc 960
ttcccgatgt ctattatcgg tggtgcaaac ctgcatcgtt ggggcttcaa accgctgatc 1020
agtggtggtt ttgctgccac tgccgttggc atcgccctgt gtatttgggg cgcgactcat 1080
actgatggtt tgccgttttt catcgcgggt ctattcttca tgggcgcggg tgctggttcg 1140
gtaatgtctg tgtcttccac tgcgattatc ggttccgcgc cggtgcgtaa ggctggcatg 1200
gcgtcgtcga tcgaagaggt ctcttatgag ttcggcacgc tgttgtctgt cgcgattttg 1260
ggtagcttgt tcccattctt ctactcgctg catgccccgg cagaggttgc ggataacttc 1320
tcggcgggtg ttcaccacgc gattgatggc gatgcggcgc gtgcatcttt ggacaccgca 1380
tacattaacg tgttgatcat tgccctagta tgcgcagtag cggctgctct gatcagcagt 1440
tacctttttcc gcggaaatcc gaagggagcc aataatgcgc actag 1485

<210> SEQ ID NO 41
<211> LENGTH: 494
<212> TYPE: PRT
<213> ORGANISM: Corynebacterium glutamicum ATCC13869

<400> SEQUENCE: 41

Met Ile Ser Glu Thr Leu Gln Ala Gln Ala Pro Thr Lys Thr Gln Arg
1 5 10 15

Trp Ala Phe Leu Ala Val Ile Ser Gly Gly Leu Phe Leu Ile Gly Val
20 25 30

Asp Asn Ser Ile Leu Tyr Thr Ala Leu Pro Leu Leu Arg Glu Gln Leu
35 40 45

Ala Ala Thr Glu Thr Gln Ala Leu Trp Ile Ile Asn Ala Tyr Pro Leu
50 55 60

Leu Met Ala Gly Leu Leu Leu Gly Thr Gly Thr Leu Gly Asp Lys Ile
65 70 75 80

Gly His Arg Arg Met Phe Leu Met Gly Leu Ser Ile Phe Gly Ile Ala
85 90 95

Ser Leu Gly Ala Ala Phe Ala Pro Thr Ala Trp Ala Leu Val Ala Ala
100 105 110

Arg Ala Phe Leu Gly Ile Gly Ala Ala Thr Met Met Pro Ala Thr Leu

-continued

```
        115                 120                 125

Ala Leu Ile Arg Ile Thr Phe Glu Asp Glu Arg Glu Arg Asn Thr Ala
    130                 135                 140

Ile Gly Ile Trp Gly Ser Val Ala Ile Leu Gly Ala Ala Ala Gly Pro
145                 150                 155                 160

Ile Ile Gly Gly Ala Leu Leu Glu Phe Phe Trp Trp Gly Ser Val Phe
                165                 170                 175

Leu Ile Asn Val Pro Val Ala Val Ile Ala Leu Ile Ala Thr Leu Phe
            180                 185                 190

Val Ala Pro Ala Asn Ile Ala Asn Pro Ser Lys His Trp Asp Phe Leu
        195                 200                 205

Ser Ser Phe Tyr Ala Leu Leu Thr Leu Ala Gly Leu Ile Val Thr Ile
    210                 215                 220

Lys Glu Ser Val Asn Thr Ala Arg His Leu Pro Leu Leu Val Gly Ala
225                 230                 235                 240

Ile Ile Leu Leu Ile Ile Gly Ala Val Leu Phe Ser Ser Arg Gln Lys
                245                 250                 255

Lys Ile Glu Glu Pro Leu Leu Asp Leu Ser Leu Phe Arg Asn Arg Leu
            260                 265                 270

Phe Leu Gly Gly Val Val Ala Ala Gly Met Ala Met Phe Thr Val Ser
        275                 280                 285

Gly Leu Glu Met Thr Thr Ser Gln Arg Phe Gln Leu Ser Val Gly Phe
    290                 295                 300

Thr Pro Leu Glu Ala Gly Leu Leu Met Ile Pro Ala Ala Leu Gly Ser
305                 310                 315                 320

Phe Pro Met Ser Ile Ile Gly Gly Ala Asn Leu His Arg Trp Gly Phe
                325                 330                 335

Lys Pro Leu Ile Ser Gly Gly Phe Leu Ala Thr Ala Val Gly Ile Ala
            340                 345                 350

Leu Cys Ile Trp Gly Ala Thr His Thr Asp Gly Leu Pro Phe Phe Ile
        355                 360                 365

Ala Gly Leu Phe Phe Met Gly Ala Gly Ala Gly Ser Val Met Ser Val
    370                 375                 380

Ser Ser Thr Ala Ile Ile Gly Ser Ala Pro Val Arg Lys Ala Gly Met
385                 390                 395                 400

Ala Ser Ser Ile Glu Glu Val Ser Tyr Glu Phe Gly Thr Leu Leu Ser
                405                 410                 415

Val Ala Ile Leu Gly Ser Leu Phe Pro Phe Phe Tyr Ser Leu His Ala
            420                 425                 430

Pro Ala Glu Val Ala Asp Asn Phe Ser Ala Gly Val His His Ala Ile
        435                 440                 445

Tyr Gly Asp Ala Ala Arg Ala Ser Leu Asp Thr Ala Tyr Ile Asn Val
    450                 455                 460

Leu Ile Ile Ala Leu Val Cys Ala Val Ala Ala Ala Leu Ile Ser Ser
465                 470                 475                 480

Tyr Leu Phe Arg Gly Asn Pro Lys Gly Ala Asn Asn Ala His
                485                 490
```

<210> SEQ ID NO 42
<211> LENGTH: 1485
<212> TYPE: DNA
<213> ORGANISM: Corynebacterium glutamicum ATCC13869

<400> SEQUENCE: 42

-continued

```
atgatttcag aaactttgca ggcgcaagcg cctacgaaaa cccaacgttg ggctttcctc     60

gctgttatca gcggtggtct ctttctgatc ggtgtagaca actcaatcct ctacaccgca    120

ctccccctgc tgcgtgaaca actcgcagcc actgaaaccc aagcgttgtg gatcatcaac    180

gcatatcccc tgctcatggc gggtcttctt ttgggtaccg gcactttggg tgacaaaatc    240

ggccaccgcc ggatgttcct catgggcttg agcattttcg gaatcgcttc acttggcgct    300

gcgtttgctc caactgcgtg ggctcttgtt gctgcgagag ctttccttgg catcggtgcg    360

gcgacgatga tgcccgcaac cttggctctg atccgcatta cgtttgaaga tgaacgcgaa    420

cggaacaccg cgattggcat ttggggttct gtggcaattc ttggcgcggc ggcaggtccg    480

atcattggtg gtgcgctgtt ggaattcttc tggtggggtt cggttttcct cattaacgtt    540

ccggtggctg ttatcgcgtt gatcgctacg ctttttgtgg cgccggccaa tatcgcgaat    600

ccgtccaagc actgggattt cttatcctcg ttctatgcat tgcttaccct tgcaggtttg    660

attgtcacca tcaaagaatc ggtaaacact gcacgtcatc tgccactgct tgtaggtgcc    720

atcatcttgc ttatcattgg tgcggtgttg tttagcagtc gtcagaagaa gatcgaggag    780

ccacttctag atctgtcgtt gttccgtaat cgccttttct taggcggtgt ggttgctgcg    840

ggcatggcga tgtttactgt gtccggtttg gaaatgacta cctcgcagcg tttccagttg    900

tctgtgggtt tcactccact tgaggctggt ttgctcatga tcccagctgc attgggtagc    960

ttcccgatgt ctattatcgg tggtgcaaac ttgcatcgtt ggggcttcaa accgctgatc   1020

agtggtggtt tccttgccac ggcagtcggc atcgccctgt gtatttgggg cgcgactcat   1080

actgatggtt tgccgttttt catcgcgggt ctgttcttca tgggcgcggg tgctggttcg   1140

gtaatgtctg tgtcttccac tgcgattatc ggttccgcgc cggtgcgtaa ggctggcatg   1200

gcgtcgtcga tcgaagaggt ctcttatgag ttcggcacgc tgttgtctgt cgcgattttg   1260

ggtagcttgt tcccattctt ctactcgctg catgccccgg cagaggttgc ggataacttc   1320

tcggcgggtg ttcaccacgc gatttatggc gatgcggcgc gtgcatcttt ggacaccgca   1380

tacattaacg tgttgatcat tgccctagta tgcgcagtag cggctgctct gatcagcagt   1440

taccttttcc gcggaaatcc gaagggagcc aataatgcgc actag                   1485
```

```
<210> SEQ ID NO 43
<211> LENGTH: 42
<212> TYPE: DNA
<213> ORGANISM: Artificial Sequence
<220> FEATURE:
<223> OTHER INFORMATION: sugR F1_ SalI primer

<400> SEQUENCE: 43

cttgcatgcc tgcaggtcga caggattcat ctggcatctg gc                         42


<210> SEQ ID NO 44
<211> LENGTH: 23
<212> TYPE: DNA
<213> ORGANISM: Artificial Sequence
<220> FEATURE:
<223> OTHER INFORMATION: sugR -R1 primer

<400> SEQUENCE: 44

gtcactcctt aaagcaaaaa gcc                                              23


<210> SEQ ID NO 45
<211> LENGTH: 42
<212> TYPE: DNA
<213> ORGANISM: Artificial Sequence
```

<220> FEATURE:
<223> OTHER INFORMATION: sugR -F2_GTG primer

<400> SEQUENCE: 45
tttttgcttt aaggagtgac gtgtacgcag aggagcgccg tc 42

<210> SEQ ID NO 46
<211> LENGTH: 42
<212> TYPE: DNA
<213> ORGANISM: Artificial Sequence
<220> FEATURE:
<223> OTHER INFORMATION: sugR -F2_TTG primer

<400> SEQUENCE: 46
tttttgcttt aaggagtgac ttgtacgcag aggagcgccg tc 42

<210> SEQ ID NO 47
<211> LENGTH: 42
<212> TYPE: DNA
<213> ORGANISM: Artificial Sequence
<220> FEATURE:
<223> OTHER INFORMATION: sugR -R2_BamHI primer

<400> SEQUENCE: 47
cgagctcggt acccggggat ccgcgagagt acgaagcgca gt 42

<210> SEQ ID NO 48
<211> LENGTH: 62
<212> TYPE: DNA
<213> ORGANISM: Artificial Sequence
<220> FEATURE:
<223> OTHER INFORMATION: sugR F3 primer

<400> SEQUENCE: 48
tttttgcttt aaggagtgac gaaggcaacc atgaactcta atgtacgcag aggagcgccg 60
tc 62

<210> SEQ ID NO 49
<211> LENGTH: 22
<212> TYPE: DNA
<213> ORGANISM: Artificial Sequence
<220> FEATURE:
<223> OTHER INFORMATION: sugR R primer

<400> SEQUENCE: 49
ggacttgcag tgactgtaag aa 22

<210> SEQ ID NO 50
<211> LENGTH: 46
<212> TYPE: DNA
<213> ORGANISM: Artificial Sequence
<220> FEATURE:
<223> OTHER INFORMATION: gltA F_speI primer

<400> SEQUENCE: 50
gaaggaatga gttcctcgag actagtactc ggcacccatc cttgtc 46

<210> SEQ ID NO 51
<211> LENGTH: 50
<212> TYPE: DNA
<213> ORGANISM: Artificial Sequence
<220> FEATURE:
<223> OTHER INFORMATION: gltA R_speI primer -continued

<400> SEQUENCE: 51

```
gttattagat gtcgggccca ctagtgtgct gtacatgctc cttgaaaatc            50
```

MICROORGANISMS FOR PRODUCING PUTRESCINE OR ORNITHINE AND PROCESS FOR PRODUCING PUTRESCINE OR ORNITHINE USING THEM

CROSS-REFERENCE TO RELATED APPLICATIONS

This application is a U.S. national phase application of International PCT Patent Application No. PCT/KR2016/003198, which was filed on Mar. 29, 2016, which claims priority to Korean Patent Application No. 10-2015-0090021, filed Jun. 24, 2015. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_060_01US_ST25.txt. The text file is 105 KB, was created on Dec. 22, 2017, and is being submitted electronically via EFS-Web.

TECHNICAL FIELD

The present invention relates to a recombinant microorganism for producing putrescine or ornithine, and a method for producing putrescine or ornithine using the them.

BACKGROUND ART

Putrescine is found in gram negative bacteria or fungi and present in various species in high concentration. Thus it is expected to carry out important roles in the metabolism of microorganisms. Generally, putrescine is a very important base material for the synthesis of polyamine nylon-4,6 and is mainly produced by a chemical synthesis method. The chemical synthesis method consists of a 3-step process including a catalytic oxidation reaction, a step of using a cyanide compound, and a hydrogenation reaction using high pressure hydrogen. In this regard, for the putrescine production, the development of a more environment-friendly method using biomass which can reduce energy consumption is required.

Under these circumstances, as methods for producing putrescine using a microorganism, methods for high-yield production of putrescine by transformation of *E. coli* and a microorganism of the genus *Corynebacterium* were disclosed (International Patent Publication No. WO 2006/005603; International Patent Publication No. WO 2009/125924; Qian Z D et al., *Biotechnol. Bioeng.* 104 (4): 651-662, 2009; Schneider et al., *Appl. Microbiol. Biotechnol.* 88 (4): 859-868, 2010; Schneider et al., *Appl. Microbiol. Biotechnol.* 95: 169-178, 2012).

Ornithine is a material widely found in plants, animals, and microorganisms and is used as a precursor in the biosynthesis of arginine, proline, and polyamines. Ornithine plays an important role in the pathway for excretion of urea produced from amino acids or ammonia by the ornithine cycle in the in vivo metabolism of higher animals. Ornithine is also used as nutrient supplements or pharmaceutical drugs in the industry for improving liver cirrhosis and liver function disorders. The known methods of producing ornithine include treatment of milk casein with digestive enzymes and use of transformed *E. coli* or a microorganism of the genus *Corynebacterium* (Korean Patent No. 10-1372635; T. Gotoh et al., *Bioprocess Biosyst. Eng.,* 33: 773-777, 2010).

SugR, which is a transcriptional regulator of sugar metabolism (hereinafter, SugR), is known as a transcriptional regulator in *Corynebacterium*, and there was a previous report that SugR inhibits the gene encoding PEP-protein phosphotransferase of the PTS system and the genes associated with glycolysis of sugars (V F Wendisch, et al., *J. Bacteriol.* 190: 24, 8033-8044, 2008). Citrate synthase is an enzyme that first acts on the TCA cycle and can regulate the rate thereof. There was a report that a modified strain of *Corynebacterium* with reduced GltA activity increased the production of aspartate and lysine (Shiio et al., *Agric Biol Chem.* 46; 101-107, 1982).

DISCLOSURE

Technical Problem

The present inventors have confirmed that the manipulation of sugR, the gene encoding SugR, and gltA, the gene encoding citrate synthase, improves the putrescine or ornithine productivity, thereby completing the present invention.

Technical Solution

An object of the present invention is to provide a recombinant microorganism which can produce putrescine or ornithine in high yield.

Another object of the present invention is to provide a method for producing putrescine or ornithine using the above microorganism.

Advantageous Effects

The present inventors have confirmed that simultaneously enhancing the citrate synthase (hereinafter, GltA) activity while weakening the SugR activity in a microorganism of the genus *Corynebacterium* producing putrescine or omithine increases the amount of putrescine or ornithine production. Accordingly, the microorganism of the present invention can be widely used for the industrial production of putrescine or omithine, and the microorganism can be widely used as an effective and desirable means in terms of the economical and environmental aspect to provide base material for the production of various polymer products, in which putrescine or ornithine are used as raw materials.

BEST MODE FOR CARRYING OUT INVENTION

An aspect of the present disclosure provides a modified microorganism of the genus *Corynebacterium* producing putrescine or ornithine, in which an activity of transcriptional regulator of sugar metabolism (SugR) is weakened compared to its endogenous activity, ii) an activity of citrate synthase (GltA) is enhanced compared to its endogenous activity, or iii) the activity of SugR is weakened compared to its endogenous activity and an activity of GltA is enhanced compared to its endogenous activity.

An exemplary embodiment of the present disclosure provides the modified microorganism of the genus *Corynebacterium* producing putrescine or ornithine, in which an activity of SugR is weakened compared to its endogenous activity and an activity of GltA is enhanced compared to its endogenous activity.

Another exemplary embodiment of the present disclosure provides the microorganism of the genus *Corynebacterium* producing putrescine or ornithine, in which the SugR consists of an amino acid sequence of SEQ ID NO: 1 or SEQ ID NO: 3.

Another exemplary embodiment of the present disclosure provides the microorganism of the genus *Corynebacterium* producing putrescine or ornithine, in which the GltA consists of an amino acid sequence of SEQ ID NO: 5 or SEQ ID NO: 7.

Another exemplary embodiment of the present disclosure provides the microorganism of the genus *Corynebacterium* producing putrescine or ornithine, in which the microorganism of the genus *Corynebacterium* is selected from the group consisting of *Corynebacterium glutamicum, Corynebacterium ammoniagenes, Corynebacterium thermoaminogenes, Brevibacterium flavum*, and *Brevibacterium lactofermentum*.

Another exemplary embodiment of the present disclosure provides the microorganism of the genus *Corynebacterium* producing putrescine or ornithine, in which an activity of ornithine decarboxylase (ODC) is further introduced.

Another exemplary embodiment of the present disclosure provides the microorganism of the genus *Corynebacterium* producing putrescine or ornithine, in which the ODC consists of an amino acid sequence of SEQ ID NO: 17.

Another exemplary embodiment of the present disclosure provides the microorganism of the genus *Corynebacterium* producing putrescine or ornithine, in which an activity of i) ornithine carbamoyltransferase (ArgF), ii) glutamate exporter, or iii) ornithine carbamoyltransferase and glutamate exporter is further weakened compared to its endogenous activity.

Another exemplary embodiment of the present disclosure further provides the microorganism of the genus *Corynebacterium* producing putrescine or ornithine, in which the ornithine carbamoyltransferase consists of an amino acid sequence of SEQ ID NO: 9 or SEQ ID NO: 11, and the glutamate exporter consists of an amino acid sequence of SEQ ID NO: 13 or SEQ ID NO: 15.

Another exemplary embodiment of the present disclosure provides the microorganism of the genus *Corynebacterium* producing putrescine or ornithine, in which an activity of at least one selected from the group consisting of acetyl-gamma-glutamyl-phosphate reductase (ArgC), acetylglutamate synthase or ornithine acetyltransferase (ArgJ), acetylglutamate kinase (ArgB), and acetylornithine aminotransferase (ArgD) is further enhanced compared to its endogenous activity.

Another exemplary embodiment of the present disclosure provides the microorganism of the genus *Corynebacterium* producing putrescine or ornithine, in which the acetyl-gamma-glutamyl phosphate reductase consists of an amino acid sequence of SEQ ID NO: 19 or SEQ ID NO: 21, the acetylglutamate synthase or ornithine acetyltransferase consists of an amino acid sequence of SEQ ID NO: 23 or SEQ ID NO: 25, the acetylglutamate kinase consists of an amino acid sequence of SEQ ID NO: 27 or SEQ ID NO: 29, and the acetylornithine aminotransferase consists of an amino acid sequence of SEQ ID NO: 31 or SEQ ID NO: 33.

Another exemplary embodiment of the present disclosure further provides the microorganism of the genus *Corynebacterium* producing putrescine or ornithine, in which an activity of acetyltransferase is further weakened compared to its endogenous activity.

Another exemplary embodiment of the present disclosure provides the microorganism of the genus *Corynebacterium* producing putrescine or ornithine, in which the acetyltransferase consists of an amino acid sequence of SEQ ID NO: 35 or SEQ ID NO: 37.

Another exemplary embodiment of the present disclosure provides the microorganism of the genus *Corynebacterium* producing putrescine or ornithine, in which an activity of a protein consisting of SEQ ID NO: 39 or SEQ ID NO: 41 is further enhanced compared to its endogenous activity.

Another aspect of the present disclosure provides a method for producing putrescine or ornithine, including:

(i) culturing the microorganism of the genus *Corynebacterium* producing putrescine or ornithine in a medium; and (ii) recovering putrescine or omithine from the cultured microorganism or the cultured medium in step (i).

An exemplary embodiment of the present disclosure provides the method for producing putrescine or ornithine, in which the microorganism of the genus *Corynebacterium* is *Corynebacterium glutamicum*.

Hereinafter, the present disclosure is described in detail.

An aspect of the present disclosure relates to a microorganism of the genus *Corynebacterium* producing putrescine or ornithine, in which an activity of transcriptional regulator of sugar metabolism (SugR) is weakened compared to its endogenous activity, ii) an activity of citrate synthase (GltA) is enhanced compared to its endogenous activity, or iii) the activity of SugR is weakened compared to its endogenous activity and an activity of GltA is enhanced compared to its endogenous activity. Specifically, the present disclosure relates to a microorganism of the genus *Corynebacterium* producing putrescine or ornithine, in which an activity of transcriptional regulator of sugar metabolism is weakened compared to its endogenous activity and an activity of citrate synthase is enhanced compared to its endogenous activity.

As used herein, the term "transcriptional regulator of sugar metabolism (SugR)" refers to an enzyme which broadly functions as an inhibitor regarding the genes associated with various aspects of sugar metabolism, such as sugar uptake and the phosphotransferase system, glycolysis, fermentation related to lactate dehydrogenase, etc. In the present disclosure, SugR includes both the endogenous proteins and foreign proteins within a microorganism of the genus *Corynebacterium*, and specifically, a SugR derived from a microorganism of the genus *Corynebacterium*.

In the present disclosure, the transcriptional regulator of sugar metabolism may include, without limitation, any protein including the amino acid sequence of SEQ ID NO: 1 or SEQ ID NO: 3, or any protein including an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as the transcriptional regulator of sugar metabolism.

Additionally, since the amino acid sequence of a protein encoding the above activity may differ depending on the species or strain of the microorganism, the SugR may not be limited regarding its origin in the present disclosure, but the SugR may be, for example, derived from a microorganism of the genus *Corynebacterium*, and specifically, derived from *Corynebacterium glutamicum*. It is obvious that any amino acid sequence which has a homology to the above sequences and has a biological activity substantially the same as or corresponding to the protein of SEQ ID NO: 1 or SEQ ID NO: 3 can also belong to the scope of the present disclosure, although the amino acid sequence may have a deletion, modification, substitution, or addition in part of the sequence.

The polynucleotide encoding the transcriptional regulator of sugar metabolism of the present disclosure, as long as it has an activity similar to that of the transcriptional regulator of sugar metabolism, may include any polynucleotide which encodes the protein having an amino acid sequence of SEQ ID NO: 1 or SEQ ID NO: 3, or the polynucleotides which encode proteins having a sequence homology of 70% or higher, specifically 80% or higher, more specifically 90% or higher, even more specifically 95% or higher, yet even more specifically 98% or higher, and most specifically 99% or higher to the above amino acid sequences. Regarding the polynucleotide encoding the transcriptional regulator of sugar metabolism, considering the codons based on codon degeneracy or those preferred by organisms to express the regulator, various modifications may be executed on the coding region within the scope without changing the amino acid sequence of the polypeptide, and specifically, the polynucleotide may include the polynucleotide sequence of SEQ ID NO: 2 or SEQ ID NO: 4, but is not limited thereto.

As used herein, the term "citrate synthase (GltA)" refers to an enzyme which is involved in the production of various intracellular biosynthetic intermediates and the production of reduced purine nucleic acid. GltA is known to act to mediate the hydrolytic condensation between acetyl-CoA and oxaloacetate for the production of citrate. In the present disclosure, GltA includes both the endogenous enzymes and foreign proteins present in a microorganism of the genus *Corynebacterium*, and specifically, GltA derived from a microorganism of the genus *Corynebacterium.*

In the present disclosure, GltA may include, without limitation, the proteins having the amino acid sequence of SEQ ID NO: 5 or SEQ ID NO: 7, or any protein which includes an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, and has the substantial activity of mediating the hydrolytic condensation between acetyl-CoA and oxaloacetate for the production of citrate.

Additionally, since the amino acid sequence of the protein exhibiting the activity may vary according to the species or strain of the microorganism, GltA may be derived from, for example, *Corynebacterium*, and specifically, *Corynebacterium glutamicum*, but the origin of GltA is not limited thereto in the present disclosure. It is obvious that any amino acid sequence which has a homology to the above sequences and has a biological activity substantially the same as or corresponding to the protein of SEQ ID NO: 5 or SEQ ID NO: 7 can also belong to the scope of the present disclosure, although the amino acid sequence may have a deletion, modification, substitution, or addition in part of the sequence.

The polynucleotide encoding GltA of the present disclosure may include the polynucleotides which encode the amino acid of SEQ ID NO: 5 or SEQ ID NO: 7, or the polynucleotides which encode proteins having a homology of 70% or higher, specifically 80% or higher, more specifically 90% or higher, even more specifically 95% or higher, yet even more specifically 98% or higher, and most specifically 99% or higher to the above amino acid sequences. Regarding the polynucleotide encoding GltA, considering the codons based on codon degeneracy or those preferred by organisms to express the GltA, various modifications may be executed on the coding region within the scope without changing the amino acid sequence of the polypeptide, and specifically, the polynucleotide may include the polynucleotide sequence of SEQ ID NO: 6 or SEQ ID NO: 8, but is not limited thereto.

As used herein, the term "homology" refers to a degree of identity compared with a given amino acid sequence or a polynucleotide sequence and may be indicated as a percentage. In the present disclosure, homologous sequences having the same or similar activity to that of the given amino acid sequence or the polynucleotide sequence are indicated in terms of "% homology." For example, homology may be confirmed using standard software for calculating parameters (e.g., parameters such as score, identity, and similarity), specifically BLAST 2.0, or comparing sequences by southern blot under defined stringent hybridization conditions, and the appropriate hybridization conditions to be defined may be determined by a method which is within the scope of the art and well-known to one of ordinary skill in the art (e.g., J. Sambrook et al., *Molecular Cloning, A Laboratory Manual,* 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York).

Additionally, the polynucleotides encoding SugR and citrate synthase of the present disclosure may be hybridized under stringent conditions with the polynucleotide sequences of SEQ ID NO: 2 or 4, or SEQ ID NO: 6 or 8, or probes derived from the polynucleotide sequences, respectively, and may be a modified type encoding SugR and citrate synthase which are involved in normal functions. As used herein, the term "stringent conditions" refers to a condition which enables a specific hybridization between polynucleotides. For example, the stringent conditions are specifically described in references (e.g., J. Sambrook et al., ibid).

In the present disclosure, attempts were made to weaken the activity of SugR, or to enhance the activity of GltA, or to apply both weakening of the SugR activity and enhancing of the GltA activity simultaneously to a microorganism of the genus *Corynebacterium* producing putrescine or ornithine, and as a result, it was confirmed that the amount of putrescine or ornithine production was improved in all modified strains.

In particular, the microorganism of the present disclosure may include both wild type and modified type microorganisms as long as they can produce putrescine or ornithine. For example, the microorganism may belong to the genus *Escherichia*, the genus *Shigella*, the genus *Citrobacter*, the genus *Salmonella*, the genus *Enterobacter*, the genus *Yersinia*, the genus *Klebsiella*, the genus *Erwinia*, the genus *Corynebacterium*, the genus *Brevibacterium*, the genus *Lactobacillus*, the genus *Selenomanas*, the genus *Vibrio*, the genus *Pseudomonas*, the genus *Streptomyces*, the genus *Arcanobacterium*, and the genus *Alcaligenes*. Specifically, the microorganism of the present disclosure may belong to the genus *Corynebacterium*, and more specifically, may be selected from the group consisting of *Corynebacterium glutamicum, Corynebacterium ammoniagenes, Corynebacterium thermoaminogenes, Brevibacterium flavum*, and *Brevibacterium lactofermentum*, and even more specifically, may be *Corynebacterium glutamicum*, but is not limited thereto.

Specifically, as used herein, the term "producing putrescine or ornithine" refers to a microorganism provided with putrescine or ornithine productivity in a parent strain which has the putrescine or ornithine in a natural state or has no putrescine or ornithine productivity.

Additionally, the microorganism producing putrescine or ornithine may be modified to weaken an activity of ornithine carbamoyltransferase (ArgF), which is involved in the synthesis of arginine, and/or an activity of glutamate exporter (NCgl1221), which is a protein involved in the excretion of glutamate, compared to their respective endogenous activities.

Furthermore, the microorganism having putrescine productivity may be modified to weaken the activity of acetyltransferase (NCgl1469), which is a protein that acetylates putrescine, compared to its endogenous activity and/or to introduce the activity of ODC, which is a protein that converts ornithine into putrescine.

In particular, the modification of enhancing or weakening activities may occur by a process called transformation in the present disclosure. As used herein, the term “transformation” refers to a process of introducing a polynucleotide encoding a particular protein or a vector including a promoter sequence with strong or weak activity, etc., into a host cell, thereby enabling the expression of the protein encoded by the polynucleotide in the host cell or inducing the modification of the chromosome of the host cell.

Additionally, the polynucleotide includes DNA and RNA which encode the target protein. The polynucleotide may be inserted in any form as long as it can be introduced into a host cell and expressed therein. For example, the polynucleotide may be introduced into a host cell in the form of an expression cassette, which is a gene construct including all essential elements required for self-expression. The expression cassette may conventionally include a promoter operably connected to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably connected to a sequence necessary for its expression in the host cell, but is not limited thereto.

Additionally, as used herein, the term “operably connected” refers to a functional connection between a promoter sequence, which initiates and mediates the transcription of the polynucleotide encoding the target protein of the present disclosure, and the above gene sequence.

As used herein, the term “vector” refers to any DNA construct which includes the polynucleotide sequence encoding the target protein, which is operably connected to an appropriate control sequence capable of expressing the target protein in an appropriate host cell. The control sequence includes a promoter capable of initiating transcription, any operator sequence capable of controlling the transcription, a sequence encoding an appropriate mRNA ribosome-binding domain, and sequences capable of controlling the termination of transcription and translation. The vector, after being transformed into an appropriate host cell, may be replicated or function regardless of the host genome, or may be integrated into the host genome itself.

The vector to be used in the present disclosure may not be particularly limited as long as the vector is replicable in a host cell, and any vector known in the art may be used. Examples of the vector conventionally used may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used; and as a plasmid vector, those based on pBR, pUC, pBluescriptII, pGEM, pTZ, pCL, pET, etc., may be used. The vector to be used in the present disclosure may not be particularly limited but any known expression vector may be used. Specifically, pDZ, pDZTn, pACYC177, pACYC184, pCL, pECCG117, pUC19, pBR322, pMW118, pCC1BAC vectors, etc., may be used.

As such, the polynucleotide encoding a foreign target protein may be replaced with a modified polynucleotide in the chromosome by a vector for insertion into bacterial chromosome. The insertion of the polynucleotide into the chromosome may be performed using any known method in the art, for example, by homologous recombination, but is not limited thereto. Since the vector of the present disclosure can be inserted into the chromosome by homologous recombination, a selection marker for confirmation of the insertion into the chromosome may be further included. The selection marker is used for the selection of a transformed cell, i.e., to confirm whether the target polynucleotide has been inserted, and markers capable of providing selectable phenotypes such as drug resistance, nutrient requirement, resistance to cytotoxic agents, and expression of surface proteins may be used. Under the circumstances treated with selective agents, only the cells capable of expressing the selection markers can survive or express other phenotypic traits, and thus the transformed cells can be selected.

As used herein, the term “enhancement of activity” not only includes the drawing of a higher effect than the original function due to the new introduction of an activity or an increase in the activity of a protein itself, but also includes the increase in its activity by an increase in the activity of an endogenous gene, amplification of an endogenous gene from internal or external factor(s), deletion of regulatory factor(s) for inhibiting gene expression, an increase in gene copy number, introduction of a gene from outside, modification of the expression control sequence, and specifically, an increase in enzyme activity due to replacement or modification of a promoter and a mutation within a gene, etc.

Specifically, in the present disclosure, the enhancement or increase of activity may be performed by:

1) increasing copy number of a polynucleotide encoding the enzyme,
2) modifying the expression control sequence for increasing the expression of the polynucleotide,
3) modifying the polynucleotide sequence on the chromosome for enhancing the activity of the enzyme, and
4) modifying by a combination thereof, but the method is not limited thereto.

The increase of copy number of a polynucleotide (method 1) may be performed in a form in which the polynucleotide is operably linked to a vector, or by inserting the polynucleotide into the chromosome of a host cell, although the method is not particularly limited thereto. Specifically, the increase of copy number of a polynucleotide within the chromosome of the host cell may be performed by introducing a vector which can replicate and function regardless of a host cell and to which the polynucleotide encoding the protein of the present disclosure is operably linked; or may be performed by introducing a vector which can insert the polynucleotide into the chromosome of a host cell and to which the polynucleotide is operably linked, into a host cell.

Then, the modification of the expression control sequence for increasing the expression of a polynucleotide (method 2) may be performed by inducing a modification on the polynucleotide sequence through deletion, insertion, non-conservative or conservative substitution of the polynucleotide sequence, or a combination thereof to further enhance the activity of the expression control sequence, or by replacing the polynucleotide sequence with a polynucleotide sequence having a stronger activity, although the method is not particularly limited thereto. The expression control sequence includes a promoter, an operator sequence, a sequence encoding ribosome-binding site, and a sequence regulating the termination of transcription and translation.

A strong exogenous promoter, instead of the original promoter, may be connected to the upstream region of the expression unit of the polynucleotide. Examples of the strong promoter may be CJ7 promoter, lysCP1 promoter, EF-Tu promoter, groEL promoter, aceA or aceB promoter, etc., and more specifically, the expression rate may be improved by being operably connected to *Corynebacterium*-derived lysCP1 promoter (WO 2009/096689) or CJ7 promoter (Korean Patent No. 0620092 and WO 2006/065095), but the strong promoter is not limited thereto.

Furthermore, the modification of a polynucleotide sequence on the chromosome (method 3) may be performed by inducing a modification on the expression control sequence through deletion, insertion, non-conservative or conservative substitution of the polynucleotide sequence, or a combination thereof to further enhance the activity of the polynucleotide sequence, or by replacing the polynucleotide sequence with an improved polynucleotide sequence having a stronger activity, although the method is not particularly limited thereto.

As used herein, "weakening of activity" may be achieved by deleting a part or the entirety of a polynucleotide encoding the protein to weaken the activity of the protein, by modifying the expression control sequence to reduce the expression of the polynucleotide, by modifying the polynucleotide sequence on the chromosomes to weaken the activity of the protein, and by a selected method from a combination thereof.

Specifically, in the present disclosure, the weakening of activity may be achieved by:

1) deleting a part or the entirety of a polynucleotide encoding the protein,
2) modifying the expression control sequence for reducing the expression of the polynucleotide,
3) modifying the polynucleotide sequence on the chromosomes to weaken the activity of the protein, and
4) a selected method from a combination thereof, but the method is not limited thereto.

Specifically, the method of deleting a part or the entirety of a polynucleotide encoding a protein may be performed by replacing the polynucleotide encoding the endogenous target protein within the chromosome with a polynucleotide having a partial deletion in polynucleotide sequence or a marker gene using a vector for chromosomal insertion within bacteria. As used herein, the term "a part" may vary depending on the kinds of polynucleotides, and it may specifically refer to 1 to 300, more specifically 1 to 100, and even more specifically 1 to 50.

Additionally, the method of modifying the expression control sequence may be performed by inducing a modification on the expression control sequence through deletion, insertion, non-conservative or conservative substitution of a polynucleotide sequence, or a combination thereof to further weaken the activity of the expression control sequence, or by replacing the polynucleotide sequence with a polynucleotide sequence having a weaker activity. The expression control sequence includes a promoter, an operator sequence, a sequence encoding a ribosome-binding site, and a sequence regulating the termination of transcription and translation.

Additionally, the method of modifying a polynucleotide sequence on the chromosome may be performed by inducing a modification on the polynucleotide sequence through deletion, insertion, non-conservative or conservative substitution of the polynucleotide sequence, or a combination thereof to further weaken the activity of the protein, or by replacing the polynucleotide sequence with an improved polynucleotide sequence having a stronger activity.

Additionally, the method of deleting the regulatory factor which inhibits the expression of the polynucleotide of the protein may be performed by replacing the polynucleotide for the expression inhibiting factor with a polynucleotide having a partial deletion in the polynucleotide sequence or a marker gene. As used herein, the term "a part" may vary depending on the kinds of polynucleotides, and it may specifically refer to 1 to 300, more specifically 1 to 100, and even more specifically 1 to 50.

As used herein, the term "endogenous activity" refers to an active state of an enzyme in a non-modified state, e.g., in a natural state, originally possessed by a microorganism, and the term "enhancement compared to its endogenous activity" refers to an increased state of the activity of the protein possessed by the microorganism after manipulation, such as the introduction of a gene exhibiting an activity or an increase of the copy number of the corresponding gene, deletion of the inhibition-control factor of the expression of the gene, or a modification of the expression-control sequence, e.g., the use of an improved promoter, compared to the activity possessed by the microorganism before manipulation.

The microorganism of the genus *Corynebacterium* of the present disclosure may be a microorganism of the genus *Corynebacterium* having putrescine productivity, in which the activity of ornithine decarboxylase (ODC) is further introduced.

As used herein, the term "ornithine decarboxylase (ODC)" refers to an enzyme having putrescine productivity by mediating decarboxylation of ornithine. Although the microorganism of the genus *Corynebacterium* does not have a putrescine biosynthesis pathway, when ODC is introduced from the outside, putrescine is synthesized and released extracellularly. In the present disclosure, the ODC may consist of an amino acid sequence of SEQ ID NO: 17, or may include, without limitation, any protein which has a homology of 70% or higher, specifically 80% or higher, more specifically 90% or higher, even more specifically 95% or higher, yet even more specifically 98% or higher, and most specifically 99% or higher to the above amino acid sequence, as long as the protein has substantially the same ODC activity.

Additionally, since the amino acid sequence of the protein exhibiting the activity may vary according to the species or strain of the microorganism, the origin of ODC is not limited in the present disclosure, and specifically, it may be an ODC derived from *E. coli*. It is obvious that any amino add sequence which has a homology to the above sequences and has a biological activity substantially the same as or corresponding to the protein of SEQ ID NO: 17 can also belong to the scope of the present disclosure, although the amino acid sequence may have a deletion, modification, substitution, or addition in part of the sequence.

The polynucleotide encoding ODC of the present disclosure may include the polynucleotides which encode the amino acid of SEQ ID NO: 17, or the polynucleotides which encode proteins having a homology of 70% or higher, specifically 80% or higher, more specifically 90% or higher, even more specifically 95% or higher, yet even more specifically 98% or higher, and most specifically 99% or higher to the above amino acid sequence. Regarding the polynucleotide encoding ODC, considering the codons based on codon degeneracy or those preferred by organisms to express the protein, various modifications may be executed on the coding region within the scope without changing the amino acid sequence of the polypeptide.

The microorganism of the genus *Corynebacterium* may be a microorganism of the genus *Corynebacterium* producing putrescine or ornithine, in which the activities of i) ornithine carbamoyltransferase (ArgF), ii) glutamate exporter (NCgl1221), or iii) ornithine carbamoyltransferase and glutamate exporter are further weakened compared to their endogenous activities.

In the present disclosure, the ornithine carbamoyltransferase may include, without limitation, any protein consisting of the amino acid sequence of SEQ ID NO: 9 or SEQ ID NO: 11, or any protein consisting of an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as ornithine carbamoyltransferase.

Additionally, the glutamate exporter in the present disclosure may include, without limitation, any protein consisting of the amino acid sequence of SEQ ID NO: 13 or SEQ ID NO: 15, or any protein including an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as the glutamate exporter.

Additionally, the microorganism of the genus *Corynebacterium* of the present disclosure may be a microorganism of the genus *Corynebacterium* producing putrescine or ornithine, in which at least one activity selected from the group consisting of acetyl-gamma-glutamyl phosphate reductase (ArgC), acetylglutamate synthase or ornithine acetyltransferase (ArgJ), acetylglutamate kinase (ArgB), and acetylornithine aminotransferase (ArgD) is further enhanced compared to their endogenous activities.

In the present disclosure, the acetyl-gamma-glutamyl phosphate reductase may include, without limitation, any protein consisting of the amino acid sequence of SEQ ID NO: 19 or SEQ ID NO: 21, or any protein consisting of an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as acetyl-gamma-glutamyl phosphate reductase.

Additionally, the acetylglutamate synthase or ornithine acetyltransferase may include, without limitation, any protein consisting of the amino acid sequence of SEQ ID NO: 23 or SEQ ID NO: 25, or any protein consisting of an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as acetylglutamate synthase or ornithine acetyltransferase.

In the present disclosure, the acetylglutamate kinase may include, without limitation, any protein consisting of the amino acid sequence of SEQ ID NO: 27 or SEQ ID NO: 29, or any protein consisting of an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as acetylglutamate kinase.

Additionally, in the present disclosure, the acetylornithine aminotransferase may include, without limitation, any protein consisting of the amino acid sequence of SEQ ID NO: 31 or SEQ ID NO: 33, or any protein consisting of an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as acetylornithine aminotransferase.

Furthermore, the microorganism of the genus *Corynebacterium* of the present disclosure may be a microorganism of the genus *Corynebacterium* having putrescine productivity, in which the activity of acetyltransferase (NCgl1469) is further weakened compared to its endogenous activity.

In the present disclosure, the acetyltransferase may include any protein which can transfer an acetyl group to putrescine. The acetyltransferase may include, without limitation, any protein consisting of the amino acid sequence of SEQ ID NO: 35 or SEQ ID NO: 37, or any protein consisting of an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as acetyltransferase.

Lastly, the microorganism of the genus *Corynebacterium* of the present disclosure may be a microorganism of the genus *Corynebacterium* having putrescine productivity, in which the activity of NCgl2522 is further enhanced compared to its endogenous activity.

In the present disclosure, NCgl2522 is a protein playing the role of releasing putrescine, and may include any protein which can transfer an acetyl group to putrescine. The acetyltransferase may include, without limitation, any protein consisting of the amino acid sequence of SEQ ID NO: 39 or SEQ ID NO: 41, or any protein consisting of an amino acid sequence having a sequence homology of 70% or higher, specifically 80% or higher, more specifically 90% or higher, even more specifically 95% or higher, yet even more specifically 98% or higher, and most specifically 99% or higher to the above amino acid sequences, as long as the protein has substantially the same activity as NCgl2522.

In another aspect, the present disclosure provides a method for producing putrescine or ornithine, including:

(i) culturing the microorganism of the genus *Corynebacterium* producing putrescine or ornithine in a medium; and (ii) recovering putrescine or ornithine from the cultured microorganism or the culture in step (i).

In the present disclosure, the microorganism of the genus *Corynebacterium* may be *Corynebacterium glutamicum.*

The microorganism of the genus *Corynebacterium* producing putrescine or ornithine of the present disclosure is the same as described above.

In the above method, the microorganism may be cultured by batch culture, continuous culture, and fed-batch culture known in the art, although they are not particularly limited thereto. In particular, regarding the culturing condition, proper pH (i.e. an optimal pH of 5 to 9, specifically pH 6 to 8, and most specifically pH 6.8) can be maintained using a basic chemical (e.g, sodium hydroxide, potassium hydroxide, or ammonia) or an acidic chemical (e.g., phosphoric acid or sulfuric acid), although it is not particularly limited thereto. Additionally, an aerobic condition can be maintained by adding oxygen or an oxygen-containing gas mixture to a cell culture. The culture temperature may be maintained at 20° C. to 45° C., and specifically at 25° C. to 40° C., and the microorganism may be cultured for about 10 hours to 160 hours. The putrescine or ornithine produced by the above culturing may be secreted to a culture medium or remain within the cells.

Additionally, in the culture medium, carbon sources, such as sugars and carbohydrates (e.g., glucose, sucrose, lactose, fructose, maltose, molasses, starch, and cellulose), oils and fats (e.g., soybean oil, sunflower seed oil, peanut oil, and coconut oil), fatty acids (e.g., palmitic acid, stearic acid, and linoleic acid), alcohols (e.g., glycerol and ethanol), and organic acids (e.g., acetic acid), may be used individually or in combination, but are not limited thereto nitrogen sources, such as nitrogen-containing organic compounds (e.g., peptone, yeast extract, meat juice, malt extract, corn steep liquor, soybean flour, and urea), or inorganic compounds (e.g., ammonium sulfate, ammonium chloride, ammonium phosphate, ammonium carbonate, and ammonium nitrate), may be used individually or in combination, but are not limited thereto; and potassium sources, such as potassium dihydrogen phosphate, dipotassium hydrogen phosphate, or sodium-containing salts corresponding thereto, may be used individually or in combination, but are not limited thereto. Additionally, other essential growth-stimulating substances including metal salts (e.g., magnesium sulfate or iron sulfate), amino acids, and vitamins may be contained in the medium.

The method of recovering the putrescine or ornithine produced during the culturing of the present disclosure may be performed by an appropriate culture method known in the art, for example, batch culture, continuous culture, or fed-batch culture, and thereby the target material can be recovered from the culture.

[Modes for Carrying Out Invention]

Hereinbelow, the present invention will be described in detail with accompanying exemplary embodiments. However, the exemplary embodiments disclosed herein are only for illustrative purposes and should not be construed as limiting the scope of the present invention.

Example 1

Preparation of sugR Gene-Weakened Strains from Strains Having Putrescine Productivity The present inventors have confirmed the effect of weakening of sugR, which is the gene encoding SugR, in a strain having putrescine productivity.

1-1. Preparation of sugR Gene-Weakened Strains from ATCC13032-Based Strain Having Putrescine Productivity In order to confirm whether the weakening of sugR gene is related to the putrescine productivity in a *Corynebacterium glutamicum* ATCC13032-based strain having putrescine productivity (Korean Patent Application Publication No. 10-2013-0082478), a sugR-weakened strain was prepared. Specifically, the sugR-weakened strain was prepared by changing the initiation codon of the sugR gene and replacing the promoter with B6-weakened promoter (Patek M (2005) Regulation of gene expression. In: Eggeling L, Bott M (eds) *Handbook of Corynebacterium glutamicum*. CRC, BocaRaton).

First, a vector for changing the initiation codon of the sugR gene was prepared. Regarding the vicinity of the polynucleotide sequence of the gene encoding the SugR described by SEQ ID NO: 2, the primer pairs of SEQ ID NOS: 43 and 44 for obtaining the homologous recombinant fragment upstream of the initiation codon of the sugR gene and the primer pairs of SEQ ID NOS: 45, 46 and 47 for obtaining the homologous recombinant fragment downstream of the initiation codon of the sugR gene were prepared. The primers used for the change of the initiation codons are summarized in Table 1 below.

TABLE 1

| Primer | Sequence (5'→3') |
|---|---|
| sugR F1_SalI (SEQ ID NO: 43) | CTTGCATGCCTGCAGGTCGACAGGATTCATCTG GCATCTGGC |
| sugR-R1 (SEQ ID NO: 44) | GTCACTCCTTAAAGCAAAAAGCC |
| sugR-F2_GTG (SEQ ID NO: 45) | TTTTTGCTTTAAGGAGTGACGTGTACGCAGAGG AGCGCCGTC |
| sugR-F2_TTG (SEQ ID NO: 46) | TTTTTGCTTTAAGGAGTGACTTGTACGCAGAGG AGCGCCGTC |
| sugR-R2_BamHI (SEQ ID NO: 47) | CGAGCTCGGTACCCGGGGATCCGCGAGAGTACG AAGCGCAGT |

PCR was performed using the genomic DNA of *Corynebacterium glutamicum* ATCC13032 as a template along with 2 pairs of primers, respectively, to amplify the upstream region and the downstream region of the initiation codon of sugR gene, respectively, and the resultants were subjected to electrophoresis to obtain desired fragments. In particular, PCR was performed by 30 cycles of denaturation at 95° C. for 30 seconds, annealing at 55° C. for 30 seconds, and extension at 72° C. for 30 seconds. The thus-obtained fragments were subjected to electrophoresis in a 0.8% agarose gel, and the bands of desired sizes were eluted and purified.

The pDZ vector (Korean Patent No. 10-0924065) was treated with BamHI and SalI and then the PCR products of the ATCC13032 strain were subjected to fusion cloning. The fusion cloning was performed using the In-Fusion® HD Cloning Kit (Clontech). As such, plasmids pDZ-1'sugR (GTG) and pDZ-1'sugR(TTG) were prepared.

In the case of the vector for the replacement into a B6-weakened promoter, SEQ ID NO: 48 for the vector preparation was prepared as shown in Table 2 below.

TABLE 2

| Primer | Sequence (5'→3') |
|---|---|
| sugR F3 (SEQ ID NO: 48) | TTTTTGCTTTAAGGAGTGACGAAGGCAACCATG AACTCTAATGTACGCAGAGGAGCGCCGTC |

PCR was performed using the primer pairs of SEQ ID NOS: 43 and 44 for obtaining the homologous recombinant fragment upstream of the initiation codon of the sugR gene and the primer pairs of SEQ ID NOS: 48 and 47 for obtaining the homologous recombinant fragment downstream of the initiation codon of the sugR gene, which were prepared regarding the vicinity of the polynucleotide sequence of the gene encoding the SugR described by SEQ ID NO: 2, and the upstream region and the downstream region of the initiation codon of sugR gene were amplified, respectively, and the resultants were subjected to electrophoresis to obtain desired fragments. The thus-obtained fragments were subjected to electrophoresis in a 0.8% agarose gel, and the bands of desired sizes were eluted and purified. The pDZ vector was treated with BamHI and SalI and then the PCR products of the ATCC13032 strain were subjected to fusion cloning. The fusion cloning was performed using the In-Fusion® HD Cloning Kit (Clontech). As such, the plasmidpDZ-1'sugR(B6) was prepared.

The plasmids pDZ-1'sugR(GTG), pDZ-1'sugR(TTG), and pDZ-1'sugR(B6) were introduced into a microorganism of the genus *Corynebacterium* KCCM11240P (Korean Patent Application Publication No. 10-2013-0082478) by electroporation to obtain transformants, and the transformants were plated on BHIS plate media (Braine heart infusion 37 g/L, sorbitol 91 g/L, and agar 2%) containing kanamycin (25 μg/mL) and X-gal (5-bromo-4-chloro-3-indolin-D-galactoside) and cultured to obtain colonies. Among the colonies, blue colonies were selected and thereby the strains introduced with the plasmids pDZ-1'sugR(GTG), pDZ-1'sugR (TTG), and pDZ-1'sugR(B6) were selected.

The selected strains were cultured with shaking (30° C., 8 hours) in CM medium (glucose 10 g/L, polypeptone 10 g/L, yeast extract 5 g/L, beef extract 5 g/L, NaCl 2.5 g/L, urea 2 g/L, pH 6.8) and sequentially diluted from $10^{-4}$ to $10^{-10}$, plated on a solid medium containing X-gal, and cultured to form colonies.

Among the thus-formed colonies, white colonies which appeared at a relatively low rate were selected and the strains in which the initiation codon of sugR was changed into GTG or TTG by a secondary crossover or the strains in which the promoter was changed into B6 were finally selected. Regarding the finally selected strains, PCR was performed using a primer pair of SEQ ID NOS: 43 and 47 and confirmed that the initiation codon of sugR was changed into GTG or TTG, or the promoter was converted to a B6-weakened promoter, and the modified strains of *Corynebacterium glutamicum* were named as KCCM11240P sugR (GTG), KCCM11240P sugR (TTG), KCCM11240P sugR (B6).

1-2. Preparation of a sugR Gene-Weakened Strain from an ATCC13869-Based Strain Having Putrescine Productivity DAB12-a ΔNCgl1469 (Korean Patent Application Publication No. 10-2014-0115244), which is a *Corynebacterium glutamicum* ATCC13869-based strain having putrescine productivity, was named as DAB12-b, and a sugR-weakened strain was prepared based on the DAB12-b strain.

Specifically, in order to confirm the sequences of the gene encoding SugR derived from *Corynebacterium glutamicum* ATCC13869 and the protein expressed therefrom, PCR was performed using the genomic DNA of *Corynebacterium glutamicum* ATCC13869 as a template along with a primer pair of SEQ ID NO: 43 and SEQ ID NO: 49.

TABLE 3

| Primer | Sequence (5'→3') |
|---|---|
| sugR R (SEQ ID NO: 49) | GGACTTGCAGTGACTGTAAGAA |

In particular, PCR was performed by 30 cycles of denaturation at 95° C. for 30 seconds, annealing at 55° C. for 30 seconds, and extension at 72° C. for 1 minute and 30 seconds.

The thus-obtained PCR products were separated by electrophoresis and subjected to sequence analysis, and as a result, it was confirmed that the gene encoding SugR derived from *Corynebacterium glutamicum* ATCC13869 includes a polynucleotide sequence described by SEQ ID NO: 4. The comparison of the protein sequence being encoded therefrom and the amino acid sequence of the SugR derived from *Corynebacterium glutamicum* ATCC13032 (SEQ ID NO: 1) revealed that their homology was 99%.

In order to change the initiation codon of sugR derived from *Corynebacterium glutamicum* ATCC13869 and replace the B6-weakened promoter, PCR was performed as in Example 1-1 using the genomic DNA of *Corynebacterium glutamicum* ATCC13869 as a template along with the primers described in Tables 1 and 2 above, and the PCR fragments of the upstream region and the downstream region of the initiation codon of sugR were amplified, respectively, and then subjected to electrophoresis to obtain the desired fragments. In particular, PCR was performed by 30 cycles of denaturation at 95° C. for 30 seconds, annealing at 55° C. for 30 seconds, and extension at 72° C. for 30 seconds. The thus-obtained fragments were subjected to electrophoresis in a 0.8% agarose gel, and the bands of desired sizes were eluted and purified.

The pDZ vector was treated with BamHI and SalI and then the PCR products of the ATCC13032 strain were subjected to fusion cloning. The fusion cloning was performed using the In-Fusion® HD Cloning Kit (Clontech). As such, the plasmids pDZ-2'sugR(GTG), pDZ-2'sugR (TTG), and pDZ-2'sugR(B6) were prepared.

The plasmids pDZ-2'sugR(GTG), pDZ-2'sugR(TTG), and pDZ-2'sugR(B6) were transformed into *Corynebacterium glutamicum* DAB12-b in the same manner as in Example 1-1, and the strains in which the initiation codon of sugR was changed and/or the promoter was converted to a B6-weakened promoter were selected. The thus-selected modified strains of *Corynebacterium glutamicum* were named as DAB12-b sugR(GTG), DAB12-b sugR(TTG), and DAB12-b sugR(B6), respectively.

Example 2

Preparation of a gltA-Enhanced Strain from a Strain Having Putrescine Productivity In order to confirm the effect of enhancing the activity of gltA, which is citrate synthase, in a strain having putrescine productivity, a modified strain was prepared in which gltA gene was introduced in a transposon gene within the chromosome of the strain having putrescine productivity. The pDZTn vector (WO 2009/125992) for transformation, which can introduce a gene into the chromosome, and the region of the transposon gene of the microorganism of the genus *Corynebacterium* was used.

2-1. Preparation of a gltA-Enhanced Strain from an ATCC13032-Based Strain Having Putrescine Productivity The fragments of gltA gene were amplified using the genomic DNA of *Corynebacterium glutamicum* ATCC13032 as a template along with the primers of SEQ ID NOS: 50 and 51 (Table 4). In particular, PCR was performed by 30 cycles of denaturation at 95° C. for 30 seconds, annealing at 55° C. for 30 seconds, and extension at 72° C. for 30 seconds or 1 minute and 30 seconds. The thus-obtained fragments were subjected to electrophoresis in a 0.8% agarose gel, and the bands of desired sizes were eluted and purified.

The pDZTn vector was treated with SpeI and then the PCR products were subjected to fusion cloning, respectively. The fusion cloning was performed using the In-Fusion® HD Cloning Kit (Clontech). The thus-obtained plasmid was named as pDZTn1'-gltA.

TABLE 4

| Primer | Sequence (5'→3') |
|---|---|
| gltA F_speI (SEQ ID NO: 50) | GAAGGAATGAGTTCCTCGAGACTAGTACTCGG CACCCATCCTTGTC |
| gltA R_speI (SEQ ID NO: 51) | GTTATTAGATGTCGGGCCCACTAGTGTGCTGT ACATGCTCCTTGAAAATC |

The thus-prepared plasmid was introduced into the KCCM11240P strain by electroporation to obtain a transformant, and the transformant was cultured with shaking (30° C., 8 hours) in CM medium (glucose 10 g/L, polypeptone 10 g/L, yeast extract 5 g/L, beef extract 5 g/L, NaCl 2.5 g/L, urea 2 g/L, pH 6.8), sequentially diluted from $10^{-4}$ to $10^{-10}$, plated on a solid medium containing X-gal, and cultured to form colonies.

Among the thus-formed colonies, white colonies which appeared at a relatively low rate were selected and the strain in which the gene encoding gltA was introduced by a secondary crossover was finally selected. Regarding the finally selected strain, it was confirmed that PCR was performed using a primer pair of SEQ ID NOS: 50 and 51 and that the gene encoding gltA was introduced therein, and the modified strain of *Corynebacterium glutamicum* was named as KCCM11240P Tn::gltA.

2-2. Preparation of a gltA-Enhanced Strain from an ATCC13869-Based Strain Having Putrescine Productivity Regarding the DAB12-b strain used in Example 1-2, a gltA-enhanced strain was prepared.

Specifically, in order to confirm the sequences of the gene encoding gltA derived from *Corynebacterium glutamicum* ATCC13869 and the protein expressed therefrom, PCR was performed using the genomic DNA of *Corynebacterium glutamicum* ATCC13869 as a template along with a primer pair of SEQ ID NO: 50 and SEQ ID NO: 51.

In particular, PCR was performed by 30 cycles of denaturation at 95° C. for 30 seconds, annealing at 55° C. for 30 seconds, and extension at 72° C. for 1 minute and 30 seconds. The thus-obtained PCR products were separated by electrophoresis and subjected to sequence analysis, and as a result, it was confirmed that the gene encoding gltA derived from *Corynebacterium glutamicum* ATCC13869 includes a polynucleotide sequence described by SEQ ID NO: 8. The comparison of the protein sequence being encoded therefrom and the amino acid sequence of the gltA derived from *Corynebacterium glutamicum* ATCC13032 (SEQ ID NO: 5) revealed that their homology was 99%.

In order to enhance the gltA derived from *Corynebacterium glutamicum* ATCC13869, PCR was performed as in Example 2-1 using the genomic DNA of *Corynebacterium glutamicum* ATCC13869 as a template along with the primers of SEQ ID NOS: 50 and 51 to amplify fragments of the gene. In particular, PCR was performed by 30 cycles of denaturation at 95° C. for 30 seconds, annealing at 55° C. for 30 seconds, and extension at 72° C. for 30 seconds or 1 minute and 30 seconds. The thus-obtained PCR fragments were subjected to electrophoresis in a 0.8% agarose gel, and the bands of desired sizes were eluted and purified.

The pDZTn vector was treated with SpeI and then the PCR products were subjected fusion cloning, respectively. The fusion cloning was performed using the In-Fusion® HD Cloning Kit (Clontech). The thus-obtained plasmid was named as pDZTn2'-gltA. The plasmid pDZTn2'-gltA was transformed into the *Corynebacterium glutamicum* DAB12-b strain in the same manner as in Example 2-1 and thereby the strain in which gltA was enhanced was selected. The thus-selected modified strain of *Corynebacterium glutamicum* was named as DAB12-b Tn:gltA.

Example 3

Preparation of Strains Having Putrescine Productivity with the Integration of sugR-Weakening and gltA-Enhancement and Confirmation of the Putrescine Productivity of the Strains In order to confirm the improvement of putrescine productivity of the sugR-weakened strains prepared in Examples 1-1 and 1-2 by the insertion of the gltA gene, the gltA gene was introduced into the transposon gene. In particular, the vectors pDZTn1'-gltA and pDZTn2'-gltA prepared in Examples 2-1 and 2-2 were used.

Specifically, the plasmid pDZTn1'-gltA was transformed into *Corynebacterium glutamicum* KCCM11240P sugR (GTG), -KCCM11240P sugR(TTG), and -KCCM11240P sugR(B6) in the same manner as in Example 2-1 to prepare gltA-enhanced strains. The thus-prepared modified strains of *Corynebacterium glutamicum* were named as KCCM11240P sugR(GTG) Tn::gltA, KCCM11240P sugR (TTG) Tn::gltA, and KCCM11240P sugR(B6) Tn::gltA, respectively, and among them, KCCM11240P sugR(TTG) Tn::gltA (*Corynebacterium glutamicum* CC01-1147) was deposited with the Korean Culture Center of Microorganisms (KCCM) on Nov. 28, 2014, under the accession number KCCM11615P.

Additionally, the plasmid pDZTn2'-gltA was transformed into *Corynebacterium glutamicum* DAB12-b sugR(GTG), -DAB12-b sugR(TTG), and -DAB12-b sugR(B6) in the same manner as in Example 2-2 to prepare gltA-enhanced strains. The thus-prepared modified strains of *Corynebacterium glutamicum* were named as DAB12-b sugR(GTG) Tn: gltA, DAB12-b sugR(TTG) Tn::gltA, and DAB12-b sugR (B6) Tn::gltA, respectively.

Example 4

Evaluation of Putrescine Productivity of Strains Having Putrescine Productivity with the Integration of sugR-Weakening and gltA-Enhancement In order to confirm the effect of sugR-weakening and gltA-enhancement in strains having putrescine productivity on the production of putrescine, the putrescine productivity was compared among the modified strains of *Corynebacterium glutamicum* having putrescine productivity prepared in Examples 1, 2, and 3.

Specifically, 6 different kinds of modified strains of *Corynebacterium glutamicum*, i.e., (KCCM11240P sugR (GTG) Tn::gltA/KCCM11240P sugR (TTG) Tn::gltA/ KCCM11240P sugR (B6) Tn::gltA/DAB12-b sugR (GTG) Tn::gltA/DAB12-b sugR (TTG) Tn::gltA, and DAB12-b sugR (B6) Tn::gltA)), and 2 different kinds of parent strains (i.e., KCCM11240P and DAB12-b) were respectively plated on 1 mM arginine-containing CM plate media (1% glucose, 1% polypeptone, 0.5% yeast extract, 0.5% beef extract, 0.25% NaCl, 0.2% urea, 100 µl of 50% NaOH, 2% agar, pH 6.8, based on 1 L), and cultured at 30° C. for 24 hours.

Each of the strains cultured therefrom in an amount of about one platinum loop was inoculated into 25 mL of titer medium (8% glucose, 0.25% soybean protein, 0.50% corn steep solids, 4% $(NH_4)_2SO_4$, 0.1% $KH_2PO_4$, 0.05% $MgSO_4.7H_2O$, 0.15% urea, biotin 100 g, thiamine HCl 3 mg, calcium-pantothenic acid 3 mg, nicotinamide 3 mg, 5% $CaCO_3$, based on 1 L), and cultured with shaking at 30° C. at a rate of 200 rpm for 50 hours.

In all cultures of strains, 1 mM arginine was added to the media. Upon completion of culture, the concentration of putrescine produced in each culture was measured and the results are shown in Table 5 below.

TABLE 5

| Strain | Putrescine (g/L) | Productivity (g/L/h) | Fold (%) |
|---|---|---|---|
| KCCM11240P | 5.8 | 0.116 | 100 |
| KCCM11240P sugR (TTG) | 6.3 | 0.126 | 109 |
| KCCM11240P sugR (GTG) | 6.3 | 0.126 | 109 |
| KCCM11240P sugR (B6) | 6.0 | 0.120 | 103 |
| KCCM11240P Tn::gltA | 6.2 | 0.124 | 107 |
| KCCM11240P sugR (TTG) Tn::gltA | 6.8 | 0.136 | 117 |
| KCCM11240P sugR (GTG) Tn::gltA | 6.5 | 0.130 | 112 |
| KCCM11240P sugR (B6) Tn::gltA | 6.3 | 0.126 | 109 |
| DAB12-b | 6.5 | 0.129 | 100 |
| DAB12-b sugR (TTG) | 6.9 | 0.138 | 107 |
| DAB12-b sugR (GTG) | 6.8 | 0.136 | 105 |
| DAB12-b sugR (B6) | 6.7 | 0.134 | 104 |
| DAB12-b Tn::gltA | 7.0 | 0.140 | 109 |
| DAB12-b sugR (TTG) Tn::gltA | 7.3 | 0.146 | 113 |
| DAB12-b sugR (GTG) Tn::gltA | 7.1 | 0.142 | 110 |
| DAB12-b sugR (B6) Tn::gltA | 7.1 | 0.142 | 110 |

As shown in Table 5 above, the modified strains of *Corynebacterium glutamicum* with weakened sugR or enhanced gltA showed an increase in the putrescine productivity compared to the non-modified strain, KCCM11240P, by 3% to 9%, and also, the modified strains of *Corynebacterium glutamicum* with simultaneously weakened sugR and enhanced gltA showed an increase in the putrescine productivity by 9% to 17%.

Additionally, the modified strains of the DAB12-b strain with weakened sugR or enhanced gltA showed an increase in the putrescine productivity compared to the non-modified strain, by 4% to 9% and also, the modified strains of the DAB12-b strain with simultaneously weakened sugR and enhanced gltA showed an increase in the putrescine productivity by 10% to 13%.

Example 5

Preparation of Strains with Increased Ability of Putrescine Secretion Based on Strains Having Putrescine Productivity with Integration of sugR-Weakening and gltA-Enhancement and Confirmation of Putrescine Productivity of the Strains 5-1. Preparation of Strains with Increased Ability of Putrescine Secretion Based on Strains with Integration of sugR-Weakening and gltA-Enhancement In order to confirm whether the KCCM11401P strain with increased ability of putrescine secretion (Korean Patent Application Publication No. 10-2014-0115244) can improve the putrescine productivity by the weakening of the activity of sugR gene and the enhancement of the activity of gltA gene, modified strains were prepared.

Specifically, first, the plasmids pDZ-1'sugR(GTG), pDZ-1'sugR(TTG), and pDZ-1'sugR(B6) prepared in Example 1-1 were transformed into *Corynebacterium glutamicum* KCCM 11401P, and the strains in which the initiation codon of sugR was converted to TTG thus resulted in weakening of sugR were selected therefrom. The thus-selected modified strains of *Corynebacterium glutamicum* were named as KCCM11401P sugR(GTG), KCCM11401P sugR(TTG), and KCCM11401P sugR(B6), respectively.

Then, in order to confirm whether the putrescine productivity can be improved by the enhancement of the activity of gltA gene, the gltA gene was introduced into a transposon gene of the strains with weakened sugR gene prepared above. In particular, the vector pDZTn1'-gltA prepared in Example 2-1 was used.

Specifically, the plasmid pDZTn1'-gltA prepared in Example 2-1 was transformed into KCCM11401P sugR (GTG), KCCM11401P sugR(TTG), and KCCM11401P sugR(B6), and the gltA-enhanced strains were selected. The thus-selected modified strains of *Corynebacterium glutamicum* were named as KCCM11401P sugR(GTG) Tn::gltA, KCCM11401P sugR(TTG) Tn::gltA, and KCCM11401P sugR(B6) Tn::gltA.

5-2. Evaluation of Strains with Increased Ability of Putrescine Secretion Based on Strains Having Putrescine Productivity with Integration of sugR-Weakening and gltA-Enhancement Regarding Putrescine Productivity In order to confirm the effect of sugR-weakening and gltA-enhancement in strains having putrescine productivity regarding their production of putrescine, the putrescine productivity was compared among the modified strains of *Corynebacterium glutamicum* prepared in Example 5-1.

Specifically, 7 different kinds of modified strains of *Corynebacterium glutamicum* (i.e., (KCCM11401P sugR (GTG), KCCM11401P sugR(TTG), KCCM11401P sugR (B6), KCCM11401P Tn::gltA, KCCM11401P sugR(GTG) Tn::gltA, KCCM11401P sugR(TTG) Tn::gltA, and KCCM11401P sugR(B6) Tn::gltA) and a single parent strain (KCCM11401P) were respectively plated on 1 mM arginine-containing CM plate media (1% glucose, 1% polypeptone, 0.5% yeast extract, 0.5% beef extract, 0.25% NaCl, 0.2% urea, 100 µl of 50% NaOH, 2% agar, pH 6.8, based on 1 L), and cultured at 30° C. for 24 hours.

Each of the strains cultured therefrom in an amount of about one platinum loop was inoculated into 25 mL of titer medium (8% glucose, 0.25% soybean protein, 0.50% corn steep solids, 4% $(NH_4)_2SO_4$, 0.1% $KH_2PO_4$, 0.05% $MgSO_4.7H_2O$, 0.15% urea, biotin 100 g, thiamine HCl 3 mg, calcium-pantothenic acid 3 mg, nicotinamide 3 mg, 5% $CaCO_3$ 1 L, based on 1 L), and cultured with shaking at 30° C. at a rate of 200 rpm for 50 hours.

TABLE 6

| Strain | Putrescine (g/L) | Productivity (g/L/h) | Fold (%) |
|---|---|---|---|
| KCCM11401P | 5.3 | 0.106 | 100 |
| KCCM11401P sugR (TTG) | 5.6 | 0.112 | 106 |
| KCCM11401P sugR (GTG) | 5.5 | 0.110 | 104 |
| KCCM11401P sugR (B6) | 5.4 | 0.108 | 102 |
| KCCM11401P Tn::gltA | 5.6 | 0.112 | 106 |
| KCCM11401P sugR (TTG) Tn::gltA | 6.1 | 0.122 | 115 |
| KCCM11401P sugR (GTG) Tn::gltA | 5.9 | 0.118 | 111 |
| KCCM11401P sugR (B6) Tn::gltA | 5.8 | 0.116 | 109 |

As shown in Table 6 above, the modified strains of *Corynebacterium glutamicum* with weakened sugR or enhanced gltA showed an increase in the putrescine productivity compared to the non-modified strain, KCCM11401P, by 2% to 6%, and also, the modified strains of *Corynebacterium glutamicum* with simultaneously weakened sugR and enhanced gltA showed an increase in the putrescine productivity by 9% to 15% in the putrescine productivity. It was confirmed that the results agreed with the interpretation of the results of Table 5.

Example 6

Preparation of sugR-Weakened Strains from a Strain Having Ornithine Productivity In order to confirm whether the weakening of sugR derived from *Corynebacterium glutamicum* ATCC13032 has an effect on the ornithine productivity, modified strains were prepared using the vectors prepared in Example 1-1.

The plasmids prepared in Example 1-1, i.e., pDZ-1'sugR (GTG), pDZ-1'sugR(TTG), and pDZ-1'sugR(B6), were introduced into the KCCM11137P strain (Korean Patent No. 10-1372635), which was prepared using *Corynebacterium glutamicum* ATCC13032 as the parent strain, by electroporation to obtain transformants, and the transformants were plated on BHIS plate media (Braine heart infusion 37 g/L, sorbitol 91 g/L, and agar 2%) containing kanamycin (25 μg/mL) and X-gal (5-bromo-4-chloro-3-indolin-D-galactoside) and cultured to obtain colonies. Among the colonies, blue colonies were selected and thereby the strains introduced with the plasmids pDZ-1'sugR(GTG), pDZ-1'sugR (TTG), and pDZ-1'sugR(B6) were selected.

The selected strains were cultured with shaking (30° C., 8 hours) in CM medium (glucose 10 g/L, polypeptone 10 g/L, yeast extract 5 g/L, beef extract 5 g/L, NaCl 2.5 g/L, urea 2 g/L, pH 6.8) and sequentially diluted from $10^{-4}$ to $10^{-10}$, plated on a solid medium containing X-gal, and cultured to form colonies. Among the thus-formed colonies, white colonies which appeared at a relatively low rate were selected and the strains, in which the initiation codon of sugR was changed into GTG or TTG by a secondary crossover or the strains in which the promoter was changed into B6 were finally selected. Regarding the finally selected strains, PCR was performed using a primer pair of SEQ ID NO: 43 and 47 and then it confirmed that the initiation codon of sugR was changed into GTG or TTG. The obtained modified strains of *Corynebacterium glutamicum* were named as KCCM11137P sugR(GTG), KCCM11137P sugR (TTG), and KCCM11137P sugR(B6), respectively.

Example 7

Preparation of gltA-Enhanced Strains from Strains Having Ornithine Productivity In order to confirm the effect of enhancing the gltA gene in a strain having ornithine productivity on its production of ornithine, a modified strain was prepared by inserting the gltA gene into the chromosome of the strain having ornithine productivity using the vectors prepared in Example 2-1.

Specifically, the vectors prepared in Example 2-1 were introduced into the KCCM11137P strain (Korean Patent No. 10-1372635) by electroporation to obtain transformants, and the transformants were cultured with shaking (30° C., 8 hours) in CM medium (glucose 10 g/L, polypeptone 10 g/L, yeast extract 5 g/L, beef extract 5 g/L, NaCl 2.5 g/L, urea 2 g/L, pH 6.8), sequentially diluted from $10^{-4}$ to $10^{-10}$, plated on a solid medium containing X-gal, and cultured to form colonies.

Among the thus-formed colonies, white colonies which appeared at a relatively low rate were selected and the strain in which the gene encoding gltA was introduced by a secondary crossover was finally selected. Regarding the finally selected strain, PCR was performed using a primer pair of SEQ ID NOS: 50 and 51 and confirmed that the gene encoding gltA was introduced therein, and the modified strain of *Corynebacterium glutamicum* was named as KCCM11137P Tn::gltA.

Example 8

Preparation of Strains with the Integration of sugR-Weakening and gltA-Enhancement and Confirmation of the Putrescine Productivity of the Strains 8-1. Preparation of ATCC13032-Based Strains Having Ornithine Productivity with the Integration of sugR-Weakening and gltA-Enhancement In order to confirm the effect of enhancing the activity of ornithine productivity in sugR-weakened KCCM11137P sugR(GTG), KCCM11137P sugR(TTG), and KCCM11137P sugR(B6) prepared in Example 6 by the insertion of the gltA gene into the chromosome, the gltA gene was introduced into a transposon gene. In particular, the vector pDZTn1'-gltA prepared in Example 2-1 was used.

The plasmid pDZTn1'-gltA was transformed into the *Corynebacterium glutamicum* KCCM11137P sugR TTG) in the same manner as in Example 2-1 and gltA-enhanced strains were selected. The thus-selected modified strains of *Corynebacterium glutamicum* were named as KCCM11137P sugR(GTG) Tn::gltA, KCCM11137P sugR (TTG) Tn::gltA, and KCCM11137P sugR(B6) Tn::gltA, respectively.

8-2. Evaluation of Strains with Integration of sugR-Weakening and gltA-Enhancement on Ornithine Productivity In order to confirm the effect of sugR-weakening and gltA-enhancement in strains having ornithine productivity regarding their production of ornithine, the ornithine productivity was compared among the modified strains of *Corynebacterium glutamicum* prepared in Example 8-1.

Specifically, 7 different kinds of modified strains of *Corynebacterium glutamicum* (i.e., (KCCM11137P sugR (GTG), KCCM11137P sugR(TTG), KCCM11137P sugR (B6), KCCM11137P Tn::gltA, KCCM11137P sugR(GTG) Tn::gltA, KCCM11137P sugR(TTG) Tn::gltA, and KCCM11137P sugR(B6) Tn::gltA) and a single parent strain (KCCM11137P) were respectively plated on 1 mM arginine-containing CM plate media (1% glucose, 1% polypeptone, 0.5% yeast extract, 0.5% beef extract, 0.25% NaCl, 0.2% urea, 100 μl of 50% NaOH, 2% agar, pH 6.8, based on 1 L), and cultured at 30° C. for 24 hours.

Each of the strains cultured therefrom in an amount of about one platinum loop was inoculated into 25 mL of titer medium (8% glucose, 0.25% soybean protein, 0.50% corn steep solids, 4% $(NH_4)_2SO_4$, 0.1% $KH_2PO_4$, 0.05% $MgSO_4.7H_2O$, 0.15% urea, biotin 100 g, thiamine HCl 3 mg, calcium-pantothenic acid 3 mg, nicotinamide 3 mg, 5% $CaCO_3$ based on 1 L), and cultured with shaking at 30° C. at a rate of 200 rpm for 50 hours. In all cultures of strains, 1 mM arginine was added to the media. Upon completion of culture, the concentration of ornithine produced in each culture was measured and the results are shown in Table 7 below.

TABLE 7

| Strain | Ornithine (g/L) | Productivity (g/L/h) | Fold (%) |
|---|---|---|---|
| KCCM11137P | 11.5 | 0.230 | 100 |
| KCCM11137P sugR (TTG) | 12.5 | 0.250 | 109 |
| KCCM11137P sugR (GTG) | 12.3 | 0.246 | 107 |
| KCCM11137P sugR (B6) | 12.5 | 0.250 | 109 |
| KCCM11137P Tn::gltA | 12.4 | 0.248 | 108 |
| KCCM11137P sugR (TTG) Tn::gltA | 13.5 | 0.270 | 117 |
| KCCM11137P sugR (GTG) Tn::gltA | 13 | 0.260 | 113 |
| KCCM11137P sugR (B6) Tn::gltA | 12.9 | 0.258 | 112 |

As shown in Table 7 above, the modified strains of *Corynebacterium glutamicum* with weakened sugR or enhanced gltA showed an increase in the ornithine productivity compared to the non-modified strain, KCCM11137P, by 7% to 9%, and also, the modified strains of *Corynebacterium glutamicum* with simultaneously weakened sugR and enhanced gltA showed an increase in the ornithine productivity by 12% to 17% in the ornithine productivity.

Conclusively, in a *Corynebacterium* strain producing putrescine or ornithine, it was confirmed that the production of putrescine and ornithine can be increased by weakening sugR or enhancing gltA, and when gltA was enhanced while weakening sugR, the production of putrescine and ornithine was increased more significantly.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A modified microorganism of the genus *Corynebacterium* producing putrescine, wherein an activity of transcriptional regulator of sugar metabolism (SugR) is weakened compared to its endogenous activity and an activity of citrate synthase (GltA) which is inhibited by NADH is enhanced compared to its endogenous activity.

2. The microorganism according to claim 1, wherein the transcriptional regulator of sugar metabolism consists of the amino acid sequence of SEQ ID NO: 1 or SEQ ID NO: 3.

3. The microorganism according to claim 1, wherein the citrate synthase consists of the amino acid sequence of SEQ ID NO: 5 or SEQ ID NO: 7.

4. The microorganism according to claim 1, wherein the microorganism of the genus *Corynebacterium* is selected from the group consisting of *Corynebacterium glutamicum, Corynebacterium ammoniagenes, Corynebacterium thermoaminogenes, Brevibacterium flavum*, and *Brevibacterium lactofermentum.*

5. The microorganism according to claim 1, wherein an activity of ornithine decarboxylase (ODC) is further introduced.

6. The microorganism according to claim 5, wherein the ornithine decarboxylase consists of the amino acid sequence of SEQ ID NO: 17.

7. The microorganism according to claim 1, wherein an activity of i) omithine carbamoyltransferase (ArgF), ii) glutamate exporter, or iii) ornithine carbamoyltransferase and glutamate exporter is further weakened compared to its endogenous activity.

8. The microorganism according to claim 7, wherein the omithine carbamoyltransferase consists of the amino acid sequence of SEQ ID NO: 9 or SEQ ID NO: 11, and the glutamate exporter consists of the amino acid sequence of SEQ ID NO: 13 or SEQ ID NO: 15.

9. The microorganism according to claim 1, wherein an activity of at least one selected from the group consisting of acetyl-gamma-glutamyl-phosphate reductase (ArgC), acetylglutamate synthase or ornithine acetyltransferase (ArgJ), acetylglutamate kinase (ArgB), and acetylornithine aminotransferase (ArgD) is further enhanced compared to its endogenous activity.

10. The microorganism according to claim 9, wherein the acetyl-gamma-glutamyl-phosphate reductase consists of the amino acid sequence of SEQ ID NO: 19 or SEQ ID NO: 21, the acetylglutamate synthase or ornithine acetyltransferase consists of the amino acid sequence of SEQ ID NO: 23 or SEQ ID NO: 25, the acetylglutamate kinase consists of the amino acid sequence of SEQ ID NO: 27 or SEQ ID NO: 29, and the acetylornithine aminotransferase consists of the amino acid sequence of SEQ ID NO: 31 or SEQ ID NO: 33.

11. The microorganism according to claim 1, wherein an activity of acetyltransferase is further weakened compared to its endogenous activity.

12. The microorganism according to claim 11, wherein the acetyltransferase consists of the amino acid sequence of SEQ ID NO: 35 or SEQ ID NO: 37.

13. The microorganism of claim 1, wherein an activity of a protein consisting of SEQ ID NO: 39 or SEQ ID NO: 41 is further enhanced, compared to its endogenous activity.

14. A method for producing putrescine, comprising:

(i) culturing the microorganism of the genus *Corynebacterium* according to claim 1 in a medium; and (ii) recovering putrescine from the cultured microorganism or the cultured medium.

15. The method according to claim 14, wherein the microorganism of the genus *Corynebacterium* is *Corynebacterium glutamicum.*

16. The method according to claim 14, wherein the transcriptional regulator of sugar metabolism consists of the amino acid sequence of SEQ ID NO: 1 or SEQ ID NO: 3.

17. The method according to claim 14, wherein the citrate synthase consists of the amino acid sequence of SEQ ID NO: 5 or SEQ ID NO: 7.

18. The method according to claim 14, wherein an activity of ornithine decarboxylase (ODC) is further introduced.

19. The method according to claim 14, wherein (a) an activity of i) ornithine carbamoyltransferase (ArgF), ii) glutamate exporter, or iii) ornithine carbamoyltransferase and glutamate exporter and/or (b) an activity of acetyltransferase is further weakened compared to its endogenous activity.

20. The method according to claim 14, wherein (a) an activity of at least one selected from the group consisting of acetyl-gamma-glutamyl-phosphate reductase (ArgC), acetylglutamate synthase or ornithine acetyltransferase (ArgJ), acetylglutamate kinase (ArgB), and acetylornithine aminotransferase (ArgD) and/or (b) an activity of a protein consisting of SEQ ID NO: 39 or SEQ ID NO: 41 is further enhanced compared to its endogenous activity.

21. A modified microorganism of the *Corynebacterium glutamicum* producing ornithine, wherein an activity of transcriptional regulator of sugar metabolism (SugR) is weakened compared to its endogenous activity and an activity of citrate synthase (GltA) which is inhibited by NADH is enhanced compared to its endogenous activity.

22. The microorganism according to claim 21, wherein the transcriptional regulator of sugar metabolism consists of the amino acid sequence of SEQ ID NO: 1 or SEQ ID NO: 3.

23. The microorganism according to claim 21, wherein the citrate synthase consists of the amino acid sequence of SEQ ID NO: 5 or SEQ ID NO: 7.

24. The microorganism according to claim 21, wherein an activity of i) ornithine carbamoyltransferase (ArgF), ii) glutamate exporter, or iii) ornithine carbamoyltransferase and glutamate exporter is further weakened compared to its endogenous activity.

25. The microorganism according to claim 24, wherein the ornithine carbamoyltransferase consists of the amino acid sequence of SEQ ID NO: 9 or SEQ ID NO: 11, and the glutamate exporter consists of the amino acid sequence of SEQ ID NO: 13 or SEQ ID NO: 15.

26. The microorganism according to claim 21, wherein an activity of at least one selected from the group consisting of acetyl-gamma-glutamyl-phosphate reductase (ArgC), acetylglutamate synthase or ornithine acetyltransferase (ArgJ), acetylglutamate kinase (ArgB), and acetylornithine aminotransferase (ArgD) is further enhanced compared to its endogenous activity.

27. The microorganism according to claim 26, wherein the acetyl-gamma-glutamyl-phosphate reductase consists of the amino acid sequence of SEQ ID NO: 19 or SEQ ID NO: 21, the acetylglutamate synthase or ornithine acetyltransferase consists of the amino acid sequence of SEQ ID NO: 23 or SEQ ID NO: 25, the acetylglutamate kinase consists of the amino acid sequence of SEQ ID NO: 27 or SEQ ID NO: 29, and the acetylornithine aminotransferase consists of the amino acid sequence of SEQ ID NO: 31 or SEQ ID NO: 33.

28. A method for producing ornithine, comprising:

(i) culturing the microorganism of the *Corynebacterium glutamicum* according to claim 21 in a medium; and (ii) recovering ornithine from the cultured microorganism or the cultured medium.

29. The method according to claim 28, wherein the transcriptional regulator of sugar metabolism consists of the amino acid sequence of SEQ ID NO: 1 or SEQ ID NO: 3.

30. The method according to claim 28, wherein the citrate synthase consists of the amino acid sequence of SEQ ID NO: 5 or SEQ ID NO: 7.

31. The method according to claim 28, wherein (a) an activity of i) ornithine carbamoyltransferase (ArgF), ii) glutamate exporter, or iii) ornithine carbamoyltransferase and glutamate exporter and/or (b) an activity of acetyltransferase is further weakened compared to its endogenous activity.

32. The method according to claim 28, wherein (a) an activity of at least one selected from the group consisting of acetyl-gamma-glutamyl-phosphate reductase (ArgC), acetylglutamate synthase or ornithine acetyltransferase (ArgJ), acetylglutamate kinase (ArgB), and acetylornithine aminotransferase (ArgD) and/or (b) an activity of a protein consisting of SEQ ID NO: 39 or SEQ ID NO: 41 is further enhanced compared to its endogenous activity.

* * * * *